United States Patent
Watterson et al.

(10) Patent No.: US 12,150,937 B2
(45) Date of Patent: Nov. 26, 2024

(54) NLRP3 MODULATORS

(71) Applicant: INNATE TUMOR IMMUNITY, INC., Princeton, NJ (US)

(72) Inventors: Scott Hunter Watterson, Pennington, NJ (US); Daniel O'Malley, New Hope, PA (US); Ashvinikumar V. Gavai, Princeton Junction, NJ (US); Hua Gong, King of Prussia, PA (US); Christine M. Tarby, Lawrenceville, NJ (US)

(73) Assignee: Innate Tumor Immunity, Inc., Princeton, NJ (US)

( * ) Notice: Subject to any disclaimer, the term of this patent is extended or adjusted under 35 U.S.C. 154(b) by 704 days.

(21) Appl. No.: 17/422,252

(22) PCT Filed: Jan. 20, 2020

(86) PCT No.: PCT/US2020/013263
§ 371 (c)(1),
(2) Date: Jul. 12, 2021

(87) PCT Pub. No.: WO2020/150114
PCT Pub. Date: Jul. 23, 2020

(65) Prior Publication Data
US 2022/0087991 A1  Mar. 24, 2022

Related U.S. Application Data

(60) Provisional application No. 62/791,953, filed on Jan. 14, 2019.

(51) Int. Cl.

| | |
|---|---|
| *A61K 31/4375* | (2006.01) |
| *A61K 31/444* | (2006.01) |
| *A61K 31/4709* | (2006.01) |
| *A61K 31/501* | (2006.01) |
| *A61K 31/506* | (2006.01) |
| *A61K 31/519* | (2006.01) |
| *A61K 31/553* | (2006.01) |
| *A61K 39/395* | (2006.01) |
| *A61P 35/00* | (2006.01) |
| *C07D 471/04* | (2006.01) |

(52) U.S. Cl.
CPC ........ *A61K 31/4375* (2013.01); *A61K 31/444* (2013.01); *A61K 31/4709* (2013.01); *A61K 31/501* (2013.01); *A61K 31/506* (2013.01); *A61K 31/519* (2013.01); *A61K 31/553* (2013.01); *A61K 39/3955* (2013.01); *C07D 471/04* (2013.01)

(58) Field of Classification Search
CPC .............. A61K 31/4375; A61K 31/444; A61K 31/4709; A61K 31/501; A61K 31/506; A61K 31/519; A61K 31/553; A61K 39/3955; C07D 471/04; A61P 35/00
See application file for complete search history.

(56) References Cited

U.S. PATENT DOCUMENTS

| 10,556,903 B2 * | 2/2020 | Glick ....................... A61P 37/00 |
| 11,344,543 B2 * | 5/2022 | O'Malley ............... A61P 37/00 |
| 2014/0142302 A1 * | 5/2014 | Furuyama .................. A61P 5/00 544/405 |
| 2015/0322063 A1 * | 11/2015 | Furuyama ............... A61P 25/28 546/122 |

FOREIGN PATENT DOCUMENTS

| JP | 2008519083 A | 6/2008 | |
| WO | WO-2006050843 A1 * | 5/2006 | ................ A61P 3/04 |
| WO | WO-2013060881 A1 * | 5/2013 | ........... C07D 471/04 |
| WO | 2014109414 A1 | 7/2014 | |
| WO | 2018152396 A1 | 8/2018 | |

OTHER PUBLICATIONS

Wu et. al., Bioorganic & Medicinal Chemistry Letters 25 (2015) 3251-3255 (Year: 2015).*

* cited by examiner

*Primary Examiner* — Clinton A Brooks
*Assistant Examiner* — Izabela Schmidt
(74) *Attorney, Agent, or Firm* — Jing G. Sun

(57) ABSTRACT

The present invention provides compounds of Formula (I): wherein all of the variables are as defined herein. These compounds are modulators of NLRP3, which may be used as medicaments for the treatment of proliferative disorders, such as cancer in a subject (e.g., a human).

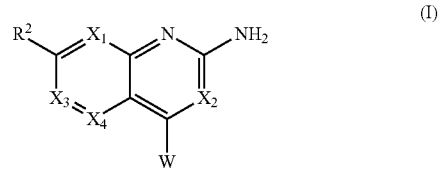

16 Claims, No Drawings

NLRP3 MODULATORS

CROSS-REFERENCE TO RELATED APPLICATIONS

This application is a 371 of International Application No. PCT/US2020/013263 filed on Jan. 13, 2020, which claims the priority benefit of U.S. Provisional Application No. 62/791,953, filed Jan. 14, 2019; the content of which is herein incorporated by reference in their entirety.

TECHNICAL FIELD

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity that contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

BACKGROUND

Nucleotide-binding oligomerization domain-like receptors ("NLRs") include a family of intracellular receptors that detect pathogen-associated molecular patterns ("PAMPs") and endogenous molecules (see, e.g., Ting, J. P. Y. et al., "The NLR gene family: a standard nomenclature," *Immunity*, 28(3):285-287, (2008)).

NLRPs represent a subfamily of NLRs that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., Chaput, C. et al., "NOD-like receptors in lung diseases," *Frontiers in Immunology*, 4: article 393, (2013)). These complexes typically include one or two NLR proteins, the adapter molecule apoptosis associated speck-like containing a CARD domain (ASC) and pro-caspase-1 F (see, e.g., Bauernfeind, F and Hornung, V. "Of inflammasomes and pathogens—sensing of microbes by the inflammasome," *EMBO Molecular Medicine*, 5(6): 814-826, (2013)).

One such inflammasome is formed by the NLRP3 scaffold, the ASC adaptor and pro-caspase-1 (see, e.g., Hirota, J. A., et al., "The airway epithelium nucleotide-binding domain and leucine-rich repeat protein 3 inflammasome is activated by urban particulate matter," *Journal of Allergy and Clinical Immunology*, 129(4):1116.e6-1125.e6, (2012)), and its expression is believed to be induced by inflammatory cytokines and TLR agonists in myeloid cells and human bronchial epithelial cells (Id.). The NLRP3 inflammasome is believed to mediate the caspase-1-dependent conversion of pro-IL-13 and pro-IL-18 to IL-1β and IL-18. Further, IL-1β and IL-18 have potential in the treatment of various types of cancer (see, e.g., Chen, L-C. et al., *EMBO Mol Med.*, 4(12):1276-1293 (2012) and Tse, B. W-C. et al., *PLoS One*, 6(9):e24241 (2011)). IL-18 has been shown to override resistance to checkpoint inhibitors in colon cancer animal tumor models (see e.g., Ma, Z. et al., *Clin. Cancer Res.* January 11. (2016) DOI: 10.1158/1078-0432.CCR-15-1655).

SUMMARY

The invention is directed to compounds of Formula (I):

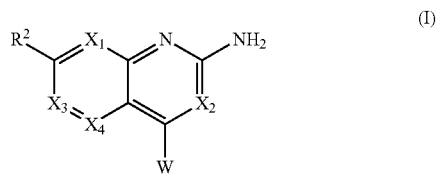

wherein all of the variables are as defined herein below.

Also within the scope of the invention are pharmaceutically acceptable salts, stereoisomers, tautomers, and solvates of the compounds of Formula (I).

The invention is also directed to pharmaceutical compositions comprising one or more compounds of the invention. The invention is also directed to methods of treating cancer using one or more compounds of the invention.

The invention also provides processes and intermediates for making the compounds of Formula (I) or pharmaceutically acceptable salts, stereoisomers, tautomers, and solvates thereof.

The compounds of the invention may be used in therapy.

The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION

Compounds of Invention

In a first aspect, the present invention provides, inter alia, a compound of Formula (I):

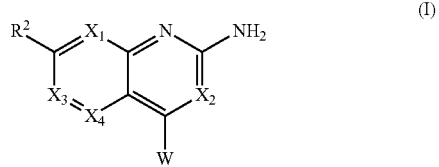

or a stereoisomer, a tautomer, or a pharmaceutically acceptable salt thereof, wherein:

W is independently selected from: —Y—$R^6$, -Q-$R^{6a}$, and $R^{6b}$;

Q is independently selected from: $NR^5$, $CHR^5$, O, and S;

Y is independently selected from: $C_{1-10}$ alkylene, $C_{2-10}$ alkenylene, and $C_{2-10}$ alkynylene, each of which is substituted with 0 to 4 $R^e$ and/or each of which is optionally interrupted by one of the following:

(i) O;
(ii) N($R^f$);
(iii) $C_{3-6}$ cycloalkylene substituted with 0 to 4 $R^g$;
(iv) phenylene further substituted with 0 to 4 $R^d$;
(v) heteroarylene including from 5 to 10 ring atoms, wherein from 1 to 4 ring atoms are each independently selected from N, N($R^f$), O, and S, and which is substituted with 0 to 4 $R^d$; or (vi) heterocycloalkylene including from 3 to 10 ring atoms, wherein from 1 to 3 ring atoms are each independently selected from N, N(R$^f$), O and S(O)$_{1-2}$, and which is substituted with 0 to 4 R$^g$;

$X_1$ and $X_2$ are, at each occurrence, independently N or CR$^1$;

$X_3$ is independently N or CR$^3$;

$X_4$ is independently N or CR$^4$;

provided that at least one of $X_1$, $X_3$ and $X_4$ is N and no more than two of $X_1$, $X_3$ and $X_4$ are N;

R$^1$ and R$^3$ are, at each occurrence, independently selected from: H, halogen, cyano, C$_{1-4}$ alkyl, C$_{1-4}$ haloalkyl, C$_{1-4}$ alkoxy, and C$_{1-4}$ haloalkoxy;

R$^2$ is independently a heteroaryl including 5 ring atoms, wherein from 1 to 4 ring atoms are each independently selected from N, NH, O, and S, wherein the heteroaryl is substituted with 0 to 3 R$^d$;

R$^4$ is independently selected from: H, halogen, cyano, C$_{1-4}$ alkyl, C$_{1-4}$ haloalkyl, C$_{1-4}$ alkoxy, C$_{1-4}$ haloalkoxy, N(C$_{1-4}$ alkyl)$_2$, and —(C$_{0-3}$ alkylene)-heteroaryl including 5 ring atoms, wherein from 1 to 4 ring atoms are each independently selected from N, NH, N(C$_{1-4}$ alkyl), O, and S, wherein the heteroaryl is substituted with 0 to 3 R$^d$;

R$^5$ is independently H or C$_{1-4}$ alkyl;

R$^6$ is independently selected from: —OR$^a$, C$_{1-4}$ haloalkoxy, —C(O)R$^a$, —CO$_2$R$^a$, —SO$_{1-2}$(R$^h$), —CONR$^i$R$^j$, cyano and R$^{6a}$;

R$^{6a}$ is independently selected from: phenyl substituted with 0 to 4 R$^d$; heteroaryl including from 5 to 10 ring atoms, wherein from 1 to 4 ring atoms are each independently selected from N, N(R$^f$), O, and S, wherein the heteroaryl is substituted with 0 to 4 R$^d$; C$_{3-10}$ cycloalkyl substituted with 0 to 4 R$^g$; and heterocyclyl including from 3 to 10 ring atoms, wherein from 1 to 3 ring atoms are each independently selected from N, N(R$^f$), O and S(O)$_{1-2}$, wherein the heterocyclyl is substituted with 0 to 4 R$^g$;

R$^{6b}$ is independently selected from: C$_{1-6}$ alkoxy, C$_{1-4}$ haloalkoxy, —C(O)R$^a$, —CO$_2$R$^a$, —SO$_{1-2}$(R$^h$), —CONR$^i$R$^j$, phenyl substituted with 0 to 4 R$^d$; heteroaryl including from 5 to 10 ring atoms, wherein from 1 to 4 ring atoms are each independently selected from N, N(R$^f$), O, and S, wherein the heteroaryl is substituted with 0 to 4 R$^d$; C$_{3-10}$ cycloalkyl substituted with 0 to 4 R$^g$; and heterocyclyl selected from

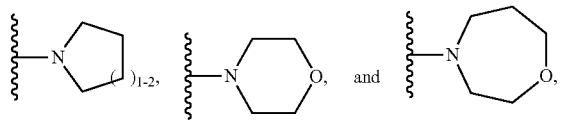

wherein the heterocyclyl is substituted with 0 to 2 R$^g$;

R$^a$ is independently selected from: H; C$_{1-8}$ alkyl substituted with 0 to 2 R$^e$; —(C$_{0-3}$ alkylene)-C$_{3-10}$ cycloalkyl, wherein the cycloalkyl is substituted with 0 to 4 R$^g$; —(C$_{0-3}$ alkylene)-heterocyclyl including from 3 to 10 ring atoms, wherein from 1 to 3 ring atoms are each independently selected from N(R$^f$), O, and S, wherein the heterocyclyl is substituted with 0 to 4 R$^g$; —(C$_{0-3}$ alkylene)-(C$_{6-10}$ aryl), wherein the aryl is substituted with 0 to 4 R$^d$; and —(C$_{0-3}$ alkylene)-heteroaryl including from 5 to 10 ring atoms, wherein from 1 to 4 ring atoms are each independently selected from N, N(R$^f$), O, and S, wherein the heteroaryl is substituted with 0 to 4 R$^d$;

R$^b$ and R$^c$ are, at each occurrence, independently R$^a$ or —C(O)R$^a$;

R$^d$ is independently selected from: halogen, OH, cyano, C$_{1-4}$ alkoxy, C$_{1-4}$ alkoxy, C$_{1-4}$ haloalkyl, C$_{1-4}$ haloalkoxy, —C(O)O(C$_{1-4}$ alkyl), NH$_2$, N(C$_{1-4}$ alkyl)$_2$, —C(O)NH$_2$, —C(O)N(C$_{1-4}$ alkyl)$_2$, C$_{2-6}$ alkenyl, C$_{2-6}$ alkynyl, and C$_{1-6}$ alkyl substituted with 0 to 2 R$^e$;

R$^e$ is independently selected from: F, OH, cyano, C$_{1-4}$ alkoxy, C$_{1-4}$ haloalkyl, C$_{1-4}$ haloalkoxy, and C$_{1-4}$ alkyl substituted with 0 to 1 R$^n$;

R$^f$ is independently selected from: H, C$_{1-4}$ alkyl substituted with 0 to 1 OH, —C(O)(C$_{1-4}$ alkyl), and —C(O)O(C$_{1-4}$ alkyl);

R$^g$ is independently oxo or R$^d$;

R$^h$ is independently selected from: C$_{1-6}$ alkyl, C$_{1-4}$ haloalkyl, —(C$_{0-3}$ alkylene)-phenyl, and —(C$_{0-3}$ alkylene)-heteroaryl including from 5 to 6 ring atoms, wherein from 1-4 ring atoms are each independently selected from N, N(R$^f$), O, and S;

R$^i$ and R$^j$ are, at each occurrence, independently H or R$^h$; or R$^i$ and R$^j$ together with the nitrogen atom to which each is attached forms a ring including from 5 to 6 ring atoms, wherein the ring includes: (a) from 3 to 5 ring carbon atoms, each of which is substituted with 1 to 2 substituents independently H and R$^m$; and (b) from 0 to 2 ring heteroatoms (in addition to the nitrogen atom attached to R$^i$ and R$^j$), which are each independently selected from N(R$^f$), O, and S;

R$^m$ is independently oxo or R$^e$; and

R$^n$ is independently selected from: OH, CONH$_2$ and C$_{1-4}$ alkoxy.

In a second aspect, within the scope of the first aspect, wherein:

Q is independently selected from: NH, N(C$_{1-4}$ alkyl), CH$_2$, and O;

Y is independently selected from: C$_{1-10}$ alkylene, C$_{2-6}$ alkenylene, and C$_{2-6}$ alkynylene, each of which is substituted with 0 to 4 R$^e$ and/or each of which is optionally interrupted by one of the following:

(i) O;

(ii) N(R$^f$);

(iii) C$_{3-6}$ cycloalkylene substituted with 0 to 4 R$^g$;

(iv) phenylene substituted with 0 to 4 R$^d$;

(v) heteroarylene including from 5 to 6 ring atoms, wherein from 1 to 4 ring atoms are each independently selected from N, N(R$^f$), O, and S, and which is substituted with 0 to 4 R$^d$; or (vi) heterocycloalkylene including from 3 to 7 ring atoms, wherein from 1 to 3 ring atoms are each independently selected from N, N(R$^f$), O and S(O)$_{1-2}$, and which is substituted with 0 to 4 R$^g$;

R$^2$ is independently 5-membered heteroaryl including from 1 to 2 ring atoms are each independently selected from N, NH, O, and S;

R$^4$ is independently selected from: H, halogen, cyano, C$_{1-4}$ alkyl, C$_{1-4}$ haloalkyl, C$_{1-4}$ alkoxy, C$_{1-4}$ haloalkoxy, N(C$_{1-4}$ alkyl)$_2$, and 5-membered heteroaryl including from 1 to 2 ring atoms are each independently selected from N, NH, O, and S;

R$^a$ is independently selected from: H, C$_{1-6}$ alkyl substituted with 0 to 2 R$^e$, and benzyl;

R$^h$ is independently C$_{1-6}$ alkyl or benzyl;

R$^i$ and R$^j$ are, at each occurrence, independently H or R$^h$.

In another aspect, within the scope of the first or second aspect, wherein:

$R^2$ is independently pyrazolyl, thienyl or isothiazolyl; and
$R^4$ is independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and heteroaryl selected from: pyrazolyl, thienyl and isothiazolyl.

In a third aspect, within the scope of the first or second aspect, the invention provides a compound of Formula (II):

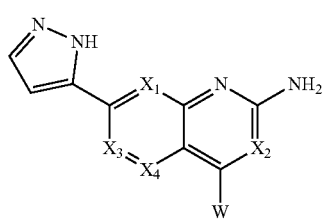

(II)

or a stereoisomer, a tautomer, or a pharmaceutically acceptable salt thereof, wherein:

W is independently selected from: —Y—$R^6$, —O—$R^{6a}$, —NH—$R^{6a}$, —O—Y—$R^6$, and $R^{6b}$;

Y is independently $C_{1-8}$ alkylene or $C_{2-6}$ alkynylene, each of which is substituted with 0 to 4 $R^e$;

$X_1$ and $X_2$ are, at each occurrence, independently N or $CR^1$;

$X_3$ is independently N or $CR^3$;

$X_4$ is independently N or $CR^4$;

provided that only one of $X_1$, $X_3$ and $X_4$ is N;

$R^1$, $R^3$ and $R^4$ are, at each occurrence, independently selected from: H, halogen and $C_{1-4}$ alkyl;

$R^6$ is independently selected from: H, OH, $C_{1-6}$ alkoxy, $N(C_{1-4}$ alkyl$)_2$, $C_{1-6}$ haloalkyl, cyano, and $R^{6a}$;

$R^{6a}$ is independently selected from: phenyl substituted with 0 to 3 $R^d$; heteroaryl including from 5 to 10 ring atoms, wherein from 1 to 4 ring atoms are each independently selected from N, N($R^f$), O, and S, wherein the heteroaryl is substituted with 0 to 3 $R^d$; $C_{3-6}$ cycloalkyl substituted with 0 to 3 $R^g$; heterocyclyl including from 3 to 8 ring atoms, wherein from 1 to 3 ring atoms are each independently selected from N, N($R^f$), O and S(O)$_{1-2}$, wherein the heterocyclyl is substituted with 0 to 3 $R^g$; and

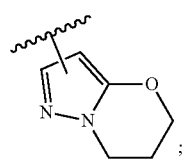

$R^{6b}$ is independently selected from: $C_{1-6}$ haloalkyl, cyano, phenyl substituted with 0 to 4 $R^d$; heteroaryl including from 5 to 10 ring atoms, wherein from 1 to 4 ring atoms are each independently selected from N, N($R^f$), O, and S, wherein the heteroaryl is substituted with 0 to 4 $R^d$; $C_{3-10}$ cycloalkyl substituted with 0 to 4 $R^g$; and heterocyclyl selected from

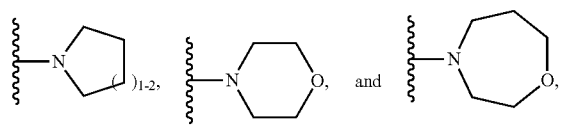

wherein the heterocyclyl is substituted with 0 to 2 $R^g$;

$R^d$ is independently selected from: halogen, cyano, OH, $CH_2OH$, $C_{1-4}$ alkoxy, $C_{1-4}$ haloalkyl, $N(C_{1-4}$ alkyl$)_2$, and $C_{1-4}$ alkyl substituted with 0 to 2 $C_{1-4}$ alkoxy;

$R^e$ is independently selected from: F, OH, —$(CH_2)_{1-4}$OH, —$CH_2CONH_2$ and $C_{1-4}$ alkyl substituted with 1 $C_{1-4}$ alkoxy;

$R^f$ is independently H or $C_{1-4}$ alkyl; and
$R^g$ is independently oxo or $R^d$.

In a fourth aspect, within the scope of any of the first to third aspects, wherein:

W is independently selected from: —Y—$R^6$, —NH—$R^{6a}$, —NH—Y—$R^6$, $R^{6b}$, and

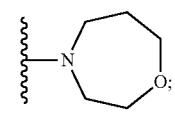

Y is independently $C_{1-6}$ alkylene substituted with 0 to 1 $R^e$;

$X^1$ and $X^2$ are, at each occurrence, independently N or CH;

$X_3$ is independently N or CH;

$X^4$ is independently N or CH;

provided that only one of $X_1$, $X^3$ and $X^4$ is N;

$R^6$ is independently selected from: H, OH, $C_{1-6}$ alkoxy, CN, $C_{1-6}$ haloalkyl, and $R^{6a}$;

$R^{6a}$ is independently selected from: pyrazolyl, pyridyl, pyrimidinyl, pyrazinyl, pyridazinyl, $C_{3-6}$ cycloalkyl and

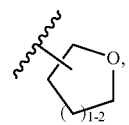

wherein each ring moiety is substituted with 0 to 2 $R^g$;

$R^{6b}$ is independently 5-membered heteroaryl, wherein from 1 to 4 ring atoms are each independently selected from N, NH, O, and S, wherein the heteroaryl is substituted with 0 to 2 $R^d$; $C_{3-6}$ cycloalkyl substituted with 0 to 2 $R^g$; and $R^e$ is independently F or OH.

In a fifth aspect, within the scope of any of the first to fourth aspects, wherein:

W is independently selected from: —NH—$R^{6a}$, —NH—Y—$R^6$,

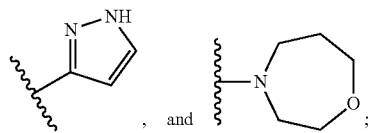 [SMILES: *c1cc[nH]n1 ; *N1CCCOCC1]

Y is independently $C_{1-4}$ alkylene;
$R^6$ is independently selected from: OH, $OCH_3$ and $R^{6a}$;
$R^{6a}$ is independently selected from: pyrazolyl, pyridyl, pyrimidinyl, cyclopentyl substituted with OH; and

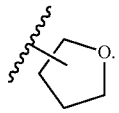

In a sixth aspect, within the scope of the fifth aspect, wherein:
W is independently selected from: —NH(CH$_2$)$_{2-4}$OH,

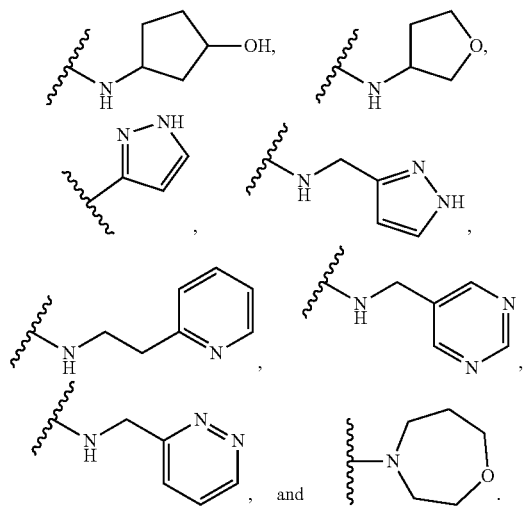

In another aspect, the invention provides a compound selected from the exemplified Examples 1 to 31 or a stereoisomer, a tautomer, or a pharmaceutically acceptable salt thereof.

In another aspect, the present invention provides a compound selected from any subset list of compounds or a single compound from the exemplified examples within the scope of any of the above aspects.

In some embodiments, $R^2$ is independently pyrazolyl, thienyl or isothiazolyl. In other embodiments, $R^2$ is pyrazolyl. In other embodiments, $R^2$ is thienyl. In other embodiments, $R^2$ is isothiazolyl.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

Other Aspects and Embodiments of the Invention

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). In preferred embodiments, methods for modulating NLRP3 activity are agonizing and partially agonizing. In certain embodiments, methods for modulating NLRP3 activity are agonizing. In certain embodiments, methods for modulating NLRP3 activity are partially agonizing. Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which an increase in NLRP3 signaling may correct a deficiency in innate immune activity that contributes to the pathology and/or symptoms and/or progression of the disease (e.g., cancer; e.g., a refractory cancer).

In some embodiments, compounds of the invention are useful for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human).

A cancer is said to be refractory when it does not respond to (or is resistant to) cancer treatment. Refractory cancer is also known as resistant cancer.

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same). In some embodiments, the cancer may be a refractory cancer.

In a further aspect, methods of treatment of a disease in which an increase in NLRP3 signaling may correct a deficiency in innate immune activity that contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which an increase in NLRP3 signaling may correct a deficiency in innate immune activity that contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which an increase in NLRP3 signaling may correct a deficiency in innate immune activity that contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof; e.g., cancer therapies that include administering one or more (e.g., two, three, four, five, six, or more) additional anti-cancer agents. Non-limiting examples of additional anti-cancer agents (chemotherapeutic agents) are selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine, Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Brentuximab vedotin, Canakinumab, Cetuximab, Certolizumab pegol, Daclizumab, Denosumab, Eculizumab, Efalizumab, Gemtuzumab, Golimumab, Ibritumomab tiuxetan, Infliximab, Ipilimumab, Muromonab-CD3, Natalizumab, Ofatumumab, Omalizumab, Palivizumab, Panitumumab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12.

The subject can have cancer; e.g., the subject has undergone and/or is undergoing and/or will undergo one or more cancer therapies.

Non-limiting examples of cancer include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In other embodiments, the mammal has been identified as having a cancer or an infectious disease. Representative infectious diseases include, without limitation, *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, *Burkholderi* infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, *Desmodesmus* infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, *Tinea barabe*, *Tinea capitis*, *Tinea corporis*, *Tinea cruris*, *Tinea manum*, *Tinea nigra*, *Tinea pedis*, *Tinea unguium*, *Tinea versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

The chemical entity can be administered intratumorally.

The chemical entity can be administered systemically (including but not limited to orally, subcutaneously, intramuscular, intravenously).

The methods can further include identifying the subject.

Other embodiments include those described in the Detailed Description and/or in the claims.

Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

For purposes of clarity and in accordance with standard convention in the art, the symbol ⊢ is used in formulas and tables to show the bond that is the point of attachment of the moiety or substituent to the core/nucleus of the structure.

Additionally, for purposes of clarity, where a substituent has a dash (—) that is not between two letters or symbols; this is used to indicate a point of attachment for a substituent. For example, —OCH$_3$ is attached through the oxygen atom.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 22nd Edition, Pharmaceutical Press, London, U K (2012); *Handbook of Pharmaceutical Excipients*, 6th ed.; Rowe et al., Eds.; The Pharmaceutical Press and the American Pharmaceutical Association: (2009); *Handbook of Pharmaceutical Additives*, 3rd ed.; Ash and Ash Eds.; Gower Publishing Company: (2007); *Pharmaceutical Preformulation and Formulation*, 2nd ed.; Gibson Ed.; CRC Press LLC: Boca Raton, FL, (2009).

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" or "halogen" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "alkylene" refers to a branched or unbranched divalent alkyl (e.g., —$CH_2$—).

The term "haloalkyl" refers to an alkyl, in which one or more hydrogen atoms is/are replaced with an independently selected halo.

The term "alkoxy" refers to an —O-alkyl radical (e.g., —$OCH_3$).

The term "haloalkoxy" refers to an —O-haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aromatic" refers generally to a ring that includes a cyclic array of resonance-stabilized 4n+2 pi electrons, wherein n is an integer (e.g., 1 or 2). Aromatic moieties include aryl and heteroaryl groups. The term "non-aromatic" describes any moiety that does not fall within the definition of "aromatic".

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkylene" as used herein refers to divalent cycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocycloalkylene" refers to divalent heterocyclyl.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The details of one or more embodiments of the invention are set forth in the accompanying drawings and the description below. Other features and advantages of the invention will be apparent from the description and drawings, and from the claims.

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) in a subject (e.g., a human). This disclosure also features compositions as well as other methods of using and making the same.

Pharmaceutical Compositions and Administration

In some embodiments, a chemical entity (e.g., a compound that modulates (e.g., agonizes or partially agonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, a pharmaceutical composition comprising a compound of the present invention or a salt thereof, and one or more pharmaceutically acceptable excipients. In certain embodiments, a pharmaceutical composition comprising a compound of the present invention or a pharmaceutically acceptable salt thereof, and one or more pharmaceutically acceptable excipients. In certain embodiments, a pharmaceutical composition comprising a therapeutically effective amount of a compound of the present invention or a pharmaceutically acceptable salt thereof, and one or more pharmaceutically acceptable excipients.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium tri silicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 10:788-795 (2006).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEGs, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 1 mg/kg; from about 0.1 mg/kg to about 0.5 mg/kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In certain embodiments, non-limiting examples of cancer include: breast cancer, colon cancer, rectal cancer, colorectal cancer, pancreatic cancer, and prostate cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

In some embodiments, the present invention provides a method of treating cancer, wherein the cancer can be any cancer that does not elicit an optimal innate immune system response.

Innate immune system refers to a part of the immune system consisting of cells that react to threats for the organism like infections or cancer in an antigen-non-specific way and stimulate the adaptive, antigen-specific immune system. In general, complete removal of the threat and long-lasting protection (=immunity) requires activity of the adaptive, antigen-specific immune system that in turn depends on stimulation by the innate immune system.

In some embodiments, the present invention provides a method of treating case, the cancer is selected based on resistance to T-cell checkpoint inhibition, either independent of cancer type and based on failure to respond to previous T-cell checkpoint inhibitor therapy or based on cancer type that is generally resistant to T-cell checkpoint inhibitor therapy such as hormone receptor positive breast cancer, microsatellite stable colon or rectal cancer, pancreatic cancer and prostate cancer.

In certain other embodiments, the present invention provides a method of treating cancer comprising an NLPR3 agonist of the present invention to treat non-inflamed tumors with low CD8+ T-cell infiltration to enhance tumor immunogenicity and promote inflammatory responses. For example, the combination may be used to treat a solid tumor based on results of a biopsy that demonstrated low CD8+ T-cell infiltration or low expression of genes produced by CD8+ T-cells.

Resistance to T-cell checkpoint inhibition refers to cancer progression on therapy or lack of response within 6 months of therapy according to consensus response criteria for the respective cancer, such as RECIST1.1 for most solid tumors.

T-cell infiltration refers to percent of T-cells of all nucleated cells by immunohistochemistry of tumor biopsy specimens.

CD8+ T-cell infiltration refers to percent of CD8+ cells of all nucleated cells by immunohistochemistry of tumor biopsy specimens.

In addition to immunohistochemistry for quantifying CD8+ T-cells in biopsy specimens, expression of genes produced by CD8+ T-cells like interferon-γ can be measured by quantifying mRNA using for example next generation sequencing and inform about CD8+ T-cell infiltration. Thresholds for low and high CD8+ T-cell infiltration by immunohistochemistry of mRNA quantifying techniques are being developed by various groups and take the spectrum of CD8+ T-cell infiltration across cancers as well as for specific cancers into account.

In any of the methods described herein, the subject can have an infectious disease. In some examples of any of the methods described herein, the subject has been identified as having an infectious disease, or has been diagnosed as having an infectious disease. For example, an infectious disease can be caused by a bacterium, virus, fungus, parasite, or a mycobacterium.

Non-limiting examples of infectious disease include: *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, *Burkholderi* infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, *Desmodesmus* infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, *Tinea barbae, Tinea capitis, Tinea corporis, Tinea cruris, Tinea manum, Tinea nigra, Tinea pedis, Tinea unguium, Tinea versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional cancer therapy comprises (chemotherapeutic agent) an immunomodulatory moiety, e.g., an immune checkpoint inhibitor. In certain of these embodiments, the immune checkpoint inhibitor targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12. See, e.g., Postow, M. *J. Clin. Oncol.* 33, 1 (2015).

In certain embodiments, the immune checkpoint inhibitor targets an immune checkpoint receptor selected from CTLA-4, PD-1, PD-L1, PD-1-PD-L1, and PD-1-PD-L2.

In certain embodiments, the immune checkpoint inhibitor is selected from: nivolumab (also known as "OPDIVO"; formerly designated 5C$_4$, BMS-936558, MDX-1106, or ONO-4538), pembrolizumab (also known as "KEYTRUDA", lambrolizumab, and MK-3475. See WO 2008/156712), PDR001 (Novartis; see WO 2015/112900), MEDI-0680 (AstraZeneca; AMP-514; see WO 2012/145493), cemiplimab (REGN-2810) (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J. Hematol. Oncol.* 10:136 (2017)), TSR-042 (ANB011; Tesaro Biopharmaceutical; see WO2014/179664), GLS-010 (WBP3055; Wuxi/Harbin Gloria Pharmaceuticals; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGD013 (Macrogenics); IBI308 (Innovent; see WO 2017/024465, WO 2017/025016, WO 2017/132825, WO2017/133540); BMS-936559 (formerly 12A4 or MDX-1105; see, e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) *J Clin Oncol* 31(suppl):3000), durvalumab (IMFINZI; MEDI-4736; AstraZeneca; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g, WO 2017/034916), CK-301 (Checkpoint Therapeutics; see Gorelik et al., AACR:Abstract 4606 (April 2016)); urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab (YERVOY; U.S. Pat. No. 6,984,720), MK-1308 (Merck), AGEN-1884 (Agenus Inc.; WO 2016/196237), and tremelimumab (formerly ticilimumab, CP-675,206; AstraZeneca; see, e.g., WO 2000/037504 and Ribas, *Update Cancer Ther.* 2(3): 133-39 (2007)).

In certain embodiments, the immune checkpoint inhibitor is selected from: nivolumab, pembrolizumab, JS001, BGB-A317, INCSHR1210, TSR-042, GLS-010, STI-1110, MGD013, IBI308, BMS-936559, atezolizumab, durvalumab, avelumab, STI-1014, CX-072, KN035, LY3300054, CK-301, urelumab, PF-05082566, MEDI6469, TRX518, varlilumab, BMS-986016, ipilimumab, AGEN-1884, and tremelimumab.

In certain of these embodiments, the immune checkpoint inhibitor is selected from: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, bevacizumab, and MNRP1685A.

In certain embodiments, the immune checkpoint inhibitor is selected from: nivolumab, ipilimumab, pembrolizumab, atezolizumab, durvalumab and avelumab.

In certain embodiments, the immune checkpoint inhibitor is selected from: nivolumab and ipilimumab.

In certain embodiments, the additional anti-cancer agent (chemotherapeutic agent) is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., —OCH$_3$ or replacement, e.g., —F or N$_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited, to Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the chemical entities, methods, and compositions described herein can be administered to certain treatment-resistant patient populations (e.g., patients resistant to checkpoint inhibitors).

In some embodiments, the compounds of the present invention may be used in therapy. In certain embodiments, the present invention provides a combined preparation of a compound of the present invention, or a pharmaceutically acceptable salt thereof, and additional therapeutic agent(s) for simultaneous, separate or sequential use in therapy.

In some embodiments, a compound of the present invention, or a pharmaceutically acceptable salt thereof, or a pharmaceutical composition containing the same, may be used as a medicament. In certain embodiments, the compounds of the invention may be used for the manufacture of a medicament for the treatment of cancer. In certain embodiments, the compounds of the invention may be used for the manufacture of a medicament for modulating NLRP3 activity. In certain embodiments, the modulating comprises agonizing NLRP3.

Methods of Preparation

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224. Synthetic chemistry transformations and protecting group methodologies (protection and deprotection) useful in synthesizing the compounds described herein are known in the art and include, for example, those such as described in Larock, R. C., *Comprehensive Organic Transformations*, $2^{nd}$ Edition, Wiley-VCH, New York, NY (1999); Wuts, P. G. M., Greene's *Protective Groups in Organic Synthesis*, 5th Edition, Wiley (2014); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

The following abbreviations have the indicated meanings:
ACN=acetonitrile
AcOH=acetic acid
BOP=(Benzotriazol-1-yloxy)tris(dimethylamino)phosphonium hexafluorophosphate
$CDCl_3$=chloroform-d
$CD_3OD$=methanol-$d_4$
$CH_2Cl_2$=dichloromethane
$CH_3ReO_3$=methyltrioxorhenium
$Cs_2CO_3$=cesium carbonate
CuI=copper (I) iodide
d=doublet
DCM=dichloromethane
DIEA=N,N-diethylisopropylamine
DMF=N,N-dimethylformamide
DMSO=dimethylsulfoxide
ES=electrospray ionization
$Et_2O$=diethyl ether
EtOAc=ethyl acetate
EtOH=ethanol
equiv=equivalents
g=gram(s)
h=hour(s)
HCl=hydrogen chloride (usually as a solution)
$H_2O$=water
$H_2O_2$=hydrogen peroxide
HATU=1-[Bis(dimethylamino)methylene]-1H-1,2,3-triazolo[4,5-b]pyridinium 3-oxide hexafluorophosphate
HPLC=high-performance liquid chromatography
$I_2$=iodine
$K_2CO_3$=potassium carbonate
$K_2HPO_4$=potassium phosphate, dibasic
KI=potassium iodide
kg=kilogram(s)
LC/MS=liquid chromatography mass spectrometer
$LiBH_4$=lithium borohydride
m=multiplet
m/z=mass to charge ratio
M=molar
m-CPBA=meta-chloroperoxybenzoic acid
mg=milligram(s)
MeOH=methanol
MHz=megahertz
mL=milliliter(s)
mmol=millimole(s)
min=minute(s)
$NaHCO_3$=sodium hydrogen carbonate
$Na_2CO_3$=sodium carbonate
NaOH=sodium hydroxide
$Na_2SO_4$=sodium sulfate
$NEt_3$ and TEA=triethylamine
$NH_4OH$ or $NH_3H_2O$=ammonium hydroxide
$NH_4HCO_3$=ammonium hydrogen carbonate
nm=nanometer
$PdCl_2(PPh_3)_2$=bis(triphenylphosphine)palladium (II) dichloride
$Pd(dppf)Cl_2$=[1,1'-Bis(diphenylphosphino)ferrocene]dichloropalladium(II)
$Pd(dppf)Cl_2DCM$=[1,1'-Bis(diphenylphosphino)ferrocene]dichloropalladium(II) dichloromethane complex
$Pd(OH)_2$=palladium hydroxide PMB=para-methoxybenzyl
POCl₃=phosphorous oxychloride
ppm=parts per million
Pt=platinum
Pt/C=platinum on carbon
s=singlet
t=triplet
TFA=trifluoroacetic acid
TLC=thin layer chromatography
TsCl=para-toluenesulfonyl chloride
° C.=degrees Celsius
µmol=micromole(s)

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention.

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be effected using the methods summarized in Schemes 1 and 2.

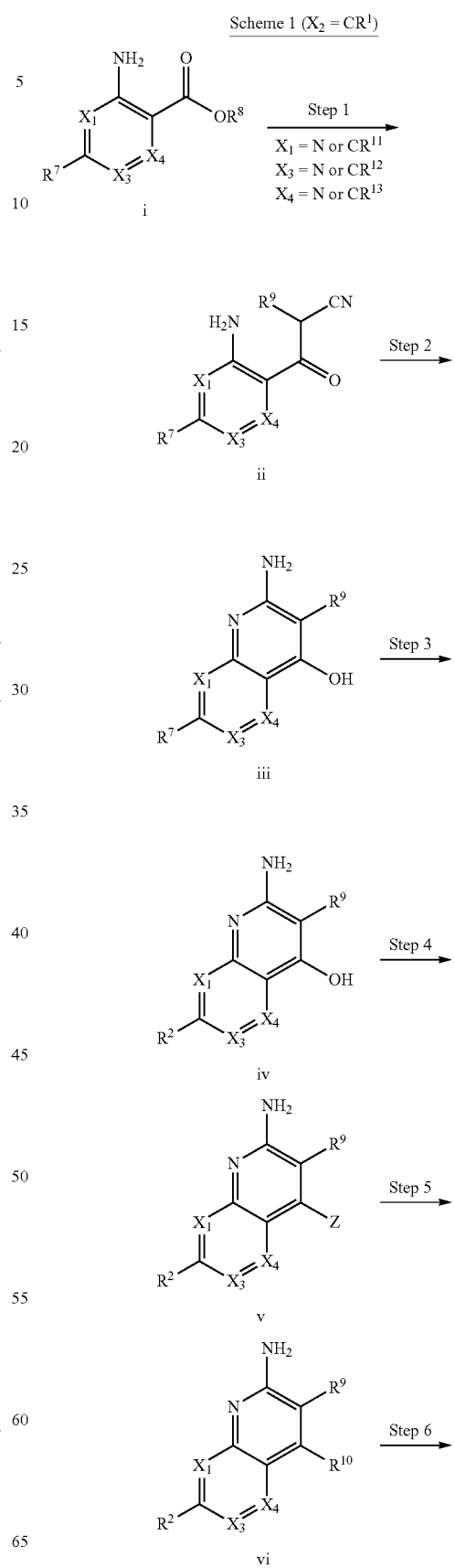

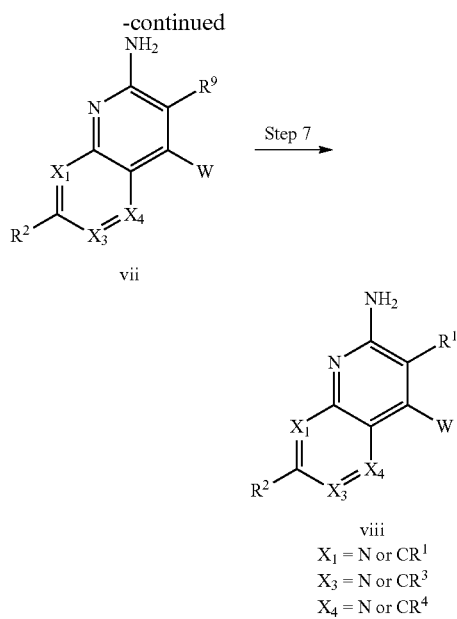

$X_1 = N$ or $CR^1$
$X_3 = N$ or $CR^3$
$X_4 = N$ or $CR^4$

Step 1: The first step of Scheme 1 begins with a suitably functionalized 2-aminonicotinate, 4-aminonicotinate, 3-aminopicolinate, or an appropriate heteroaryl ring containing multiple nitrogens (i). If desired, the groups $X_1$, $X^3$, $X^4$, and $R^7$ may be the groups $X_1$, $X^3$, $X^4$, and $R^2$ found in the final product. Alternatively, one or more of these groups may be groups that can be modified at a later stage of the synthesis, such as bromo. Starting material (i) may be purchased commercially or may be synthesized by methods known to one skilled in the art. In step 1, the ester group of compound (i) may be transformed into oxobutanitrile (ii) through a displacement with a nucleophile such as a lithiate, such as the lithiate of acetonitrile generated the addition of as base such as nBuLi in a solvent such as THF.

Step 2: In step 2 of Scheme 1, compound (ii) may be transformed into compound (iii) via a based-catalyzed cyclization with exposure of (ii) to a base such as sodium ethoxide in a solvent such as ethanol at a temperature as high as 100° C.

Steps 3 through 7 of Scheme 1 consist of a series of functional group manipulations, some optional, to convert the substituents $X_1$ (if $CR^{11}$), $X^3$ (if $CR^{12}$), $X_4$ (if $CR^{13}$), $R^7$, $R^9$, and OH in intermediate (iii) to the substituents $X_1$ (if $CR^1$), $X^3$ (if $CR^3$), $X^4$ (if $CR^4$), $R^2$, $R^1$, and W desired in the final compound (viii). One skilled in the art will recognize that some or all of these steps may not be necessary depending on the groups found in compounds (iii) and (viii). One skilled in the art will also recognize that, for some substrates, these steps may be performed in alternative order.

Step 3: Step 3 of Scheme 1 is an optional step or series of steps to transform the group $R^7$ in intermediate (iii) to the group $R^2$ found in molecule (iv). For example, if $R^7$ is bromo and the desired group $R^2$ is an aromatic or heteroaromatic group, this transformation may be effected by reacting compound (iii) with an optionally protected aromatic or heteroaromatic boronic acid or boronic ester, a catalyst such as $PdCl_2$(dppf)-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrahydropyran protecting group, the tetrahydropyran may be removed by reaction with an acid such as trifluoroacetic acid in a solvent such as dichloromethane. Alternatively, if $R^7$ is bromo and the desired group $R^2$ is an aromatic or heteroaromatic group, this transformation may be effected by reacting intermediate (iii) first with a compound such as bis(pinacolato)diboron, a reagent such as potassium acetate, and a catalyst such as $PdCl_2$(dppf)-DCM complex in a solvent such as dioxane, then reacting the resulting boronic ester with an appropriate aryl or heteroaryl halide, a base such as sodium carbonate, and a catalyst such as tetrakis (triphenylphosphine)palladium(O) in an appropriate solvent mixture such as dioxane and water. Alternatively, if $R^7$ is bromo and the desired group $R^2$ is a heterocycle linked through a nitrogen atom, this step may be effected by reaction of intermediate (iii) with the appropriate heterocycle in the presence of a copper source such as copper (I) iodide, a base such as sodium carbonate, and a ligand such as N,N'-dimethylethane-1,2-diamine in an appropriate solvent such as DMSO.

Step 4: In a step 4 of Scheme 1, the alcohol group of compound (iv) may be transformed into a halogen group or sulfonate ester, such as chloro, bromo, or triflate. If the desired group Z is chloro, this transformation may be effected by treating compound (iv) with a reagent such as phosphoryl chloride in a solvent such as toluene. Alternatively, if the desired group Z is bromo, this transformation may be effected by treating compound (iv) with a reagent such as phosphorous tribromide in a solvent such as DMF. Alternatively, if the desired group Z is triflate, this transformation may be effected by treating compound (iv) with a reagent such as trifluoromethanesulfonyl chloride, a reagent such as 4-dimethylaminopyridine, and a base such as Hunig's base in a solvent such as dichloromethane.

Step 5: In step 5 of Scheme 1, the halogen Z of compound (v) is transformed into group $R^{10}$ of compound (vi). The group $R^{10}$ may be the group W desired in the final compound; alternatively, it may be a group that can be transformed into group W at a later stage of the synthesis. One skilled in the art will recognize that the means to effect this transformation will depend on the nature of the groups $R^{10}$ and Z. For example, if Z is chloro and the desired group $R^{10}$ is an amine, this transformation may be effected by heating compound (v) to a suitable temperature, such as 120° C., with an appropriate amine and a base such as Hunig's base in solvents such as DMSO or NMP. Alternatively, if Z is chloro and the desired group $R^{10}$ is an ether, this transformation may be effected by heating compound (v) to a suitable temperature, such as 100° C., with an appropriate alcohol and a base such as potassium tert-butoxide in a solvent such as NMP. Alternatively, if Z is bromo and the desired group $R^{10}$ is an alkyne, this transformation may be effected by heating compound (v) to a suitable temperature, such as 70° C., with an appropriate alkyne, copper (I) iodide, an appropriate base, such as Hunig's base, and a suitable palladium source, such as tetrakis(triphenylphosphine)palladium(O), in a suitable solvent such as THF. Alternatively, if Z is a triflate and the desired group $R^{10}$ is a optionally substituted alkyl group, this step may be accomplished by treating compound (v) with an appropriate alkyl boronic acid or ester, a catalyst such as $PdCl_2$(dppf)-DCM complex, and a base such as cesium carbonate in a solvent such as dioxane.

Step 6: Step 6 of Scheme 1 is an optional step or series of steps to transform the group $R^{10}$ in compound (vi) to the group W found in molecule (vii). For example, if the group $R^{10}$ contains a Boc-protected amine and the desired group W contains an amide, this transformation may be accomplished by first removing the Boc group with a suitable combination of acid and solvent, such as hydrochloric acid and dioxane, then forming the desired amide by reaction with the appropriate carboxylic acid, a coupling agent such as T3P, and a base such as triethylamine in a solvent such as DMF. Alternatively, if the group $R^{10}$ contains an unsaturated group such as an alkyne, and the desired group W is fully saturated, this transformation may be effected by reaction with hydrogen and a suitable catalyst such as palladium on carbon.

Step 7: Step 7 of Scheme 1 is an optional step or series of steps to transform the groups $X_1$ (if $CR^{11}$), $X^3$ (if $CR^{12}$), $X^4$ (if $CR^{13}$), and $R^9$ in intermediate (vii) to the groups $X_1$ (if $CR^1$), $X_3$ (if $CR^3$), $X_4$ (if $CR^4$), and $R^1$ found in molecule (viii).

One skilled in the art will recognize that a number of these steps may be performed in alternative order, depending on the groups desired in the final molecule (viii). For example, for some molecules, the transformation of the group $R^7$ to $R^2$ described in Step 3 may be conducted after the transformation of the group Z to the group $R^{10}$ described in Step 5 or prior to transformation outlined in Step 1.

Scheme 2 ($X_2$ = N)

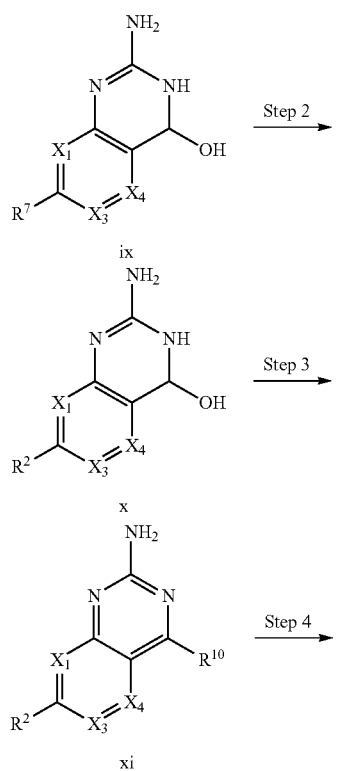

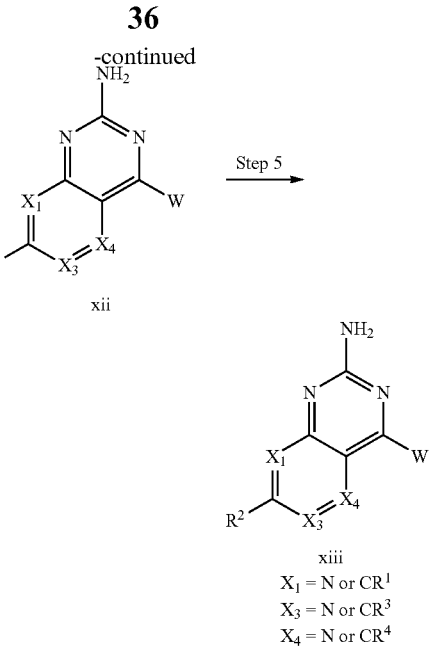

$X_1$ = N or $CR^1$
$X_3$ = N or $CR^3$
$X_4$ = N or $CR^4$

Step 1: The first step of Scheme 2 begins with a suitably functionalized 2-(halogen)nicotinate, 4-(halogen)nicotinate, 3-(halogen)picolinate, or an appropriate heteroaryl ring containing multiple nitrogens (i). If desired, the groups $X_1$, $X^3$, $X^4$, and $R_7$ may be the groups $X_1$, $X^3$, $X^4$, and $R^2$ found in the final product. Alternatively, one or more of these groups may be groups that can be modified at a later stage of the synthesis, such as bromo. Starting material (i) may be purchased commercially or may be synthesized by methods known to one skilled in the art. In step 1, compound (i) may be transformed into pyrimidinone (ix) when treated with guanidine hydrochloride in the presence of a suitable base such as NaH in a solvent such as DMA or NaOtBu in a solvent such as 2-propanol at a temperature in the range of 90–160° C.

Steps 2 through 5 of Scheme 2 consist of a series of functional group manipulations, some optional, to convert the substituents $X_1$ (if $CR^{11}$), $X^3$ (if $CR^{12}$), $X^4$ (if $CR^{13}$), $R^7$, and OH in intermediate (ix) to the substituents $X_1$ (if $CR^1$), $X^3$ (if $CR^3$), $X^4$ (if $CR^4$), $R^2$, and W desired in the final compound (xiii). One skilled in the art will recognize that some or all of these steps may not be necessary depending on the groups found in compounds (x) and (xiii). One skilled in the art will also recognize that, for some substrates, these steps may be performed in alternative order.

Step 2: Step 2 of Scheme 2 is an optional step or series of steps to transform the group $R^7$ in compound (ix) to the group $R^2$ found in molecule (x). For example, if $R^7$ is bromo and the desired group $R^2$ is an aromatic or heteroaromatic group, this transformation may be effected by reacting intermediate (ix) with an optionally protected aromatic or heteroaromatic boronic acid or boronic ester, a catalyst such as $PdCl_2(dppf)$-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrahydropyran protecting group, the tetrahydropyran may be removed by reaction with an acid such as trifluoroacetic acid in a solvent such as dichloromethane. Alternatively, if $R^7$ is bromo and the desired group $R^2$ is an aromatic or heteroaromatic group, this transformation may be effected by reacting compound (ix) first with a compound such as bis(pinacolato)diboron, a reagent such as potassium acetate, and a catalyst such as $PdCl_2$(dppf)-DCM complex in a solvent such as dioxane, then reacting the resulting boronic ester with an appropriate aryl or heteroaryl halide, a base such as sodium carbonate, and a catalyst such as tetrakis (triphenylphosphine)palladium(O) in an appropriate solvent mixture such as dioxane and water. Alternatively, if $R^7$ is bromo and the desired group $R^2$ is a heterocycle linked through a nitrogen atom, this step may be effected by reaction of intermediate (ix) with the appropriate heterocycle in the presence of a copper source such as copper (I) iodide, a base such as sodium carbonate, and a ligand such as N,N'-dimethylethane-1,2-diamine in an appropriate solvent such as DMSO.

Step 3: In step 3 of Scheme 2, the pyrimidinone of compound (x) is transformed into group $R^{10}$ of compound (xi). The group $R^{10}$ may be the group W desired in the final compound; alternatively, it may be a group that can be transformed into group W at a later stage of the synthesis. One skilled in the art will recognize that the means to effect this transformation will depend on the nature of the group $R^{10}$. For example, if the desired group $R^{10}$ is an amine, this transformation may be effected by reacting compound (x) with an appropriate amine, a coupling reagent such as BOP, and a base such as DBU in a solvent such as DMF.

Step 4: Step 4 of Scheme 2 is an optional step or series of steps to transform the group $R^{10}$ in compound (xi) to the group W found in molecule (xii). For example, if the group $R^{10}$ contains a Boc-protected amine and the desired group W contains an amide, this transformation may be accomplished by first removing the Boc group with a suitable combination of acid and solvent, such as hydrochloric acid and dioxane, then forming the desired amide by reaction with the appropriate carboxylic acid, a coupling agent such as T3P, and a base such as triethylamine in a solvent such as DMF. Alternatively, if the group $R^{10}$ contains an unsaturated group such as an alkyne, and the desired group W is fully saturated, this transformation may be effected by reaction with hydrogen and a suitable catalyst such as palladium on carbon.

Step 5: Step 5 of Scheme 2 is an optional step or series of steps to transform the groups $X_1$ (if $CR^{11}$), $X^3$ (if $CR^{12}$), and $X^4$ (if $CR^{13}$) in intermediate (xii) to the groups $X_1$ (if $CR^1$), $X^3$ (if $CR^3$), and $X^4$ (if $CR^4$) found in molecule (xiii).

One skilled in the art will recognize that a number of these steps may be performed in alternative order, depending on the groups desired in the final molecule (xiii). For example, for some molecules, the transformation of the group $R^7$ to $R^2$ described in Step 2 may be conducted after the transformation of the pyridone to the group $R^{10}$ described in Step 3.

Evaluation of Biological Activity

Measurement of IL-1β Production in PMA-Differentiated THP-1 Cells

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 μg/ml), and maintained in log phase prior to experimental setup. Prior to the experiment THP-1 were treated with PMA (Phorbol 12-myristate 13-acetate) (10 μg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×10⁶ cells/ml, and 100 μl was plated in a 96 well plate. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 4 hours. Cell free supernatant was collected and the production of IL-1β was evaluated by ELISA. A vehicle only control was run concurrently with each experiment. Final DMSO concentration was 1%. Compounds exhibit a dose-related increase of IL-1β production in PMA-differentiated THP-1 cells.

Measurement of IL-1β Production in PMA-Differentiated THP-1 Cells (Alternative Procedure)

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml), streptomycin (100 μg/ml), HEPES (10 mM) and sodium pyruvate (1 mM) and maintained in log phase prior to experimental setup. Prior to the experiment, THP-1 cells were treated with PMA (Phorbol 12-myristate 13-acetate) (20 μg/ml) overnight. The day of the experiment, the media was removed and attached cells were treated with trypsin for 2 minutes, cells were then collected, washed with PBS (phosphate buffer saline), pelleted by centrifugation and resuspended in 2% heat inactivated FBS with RPMI at a concentration of 50,000 cells/well in a 384 well plate. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 μM). Cells were incubated with compounds for 2 hours. A vehicle only control was run concurrently with each experiment. Final DMSO concentration was 1%. Compounds exhibit a dose-related increase of IL-1β production in PMA-differentiated THP-1 cells.

Measurement of IL-1β Production—hTRF Protocol (Second Alternative Procedure)

Serial dilutions of compounds in DMSO were added to low volume 384 well plates at 100 nl/well using an ECHO 550 acoustic dispenser (Labcyte) to achieve final starting concentration of 10 μM in assay.

THP-1 cells in RPMI (Gibco, 11875) media with 10% FBS at a density of 1×10⁶ cell/ml in a T175 flask were treated with a final concentration of phorbol 12-myristate 13-acetate (PMA) (Sigma, P1585) of 50 ng/ml overnight at 37° C. at 5% $CO_2$ for differentiation. Cells were harvested the next day after rinsing well wth dPBS using 0.5% trypsin. A cell solution was prepared of 1×10⁶ cells/ml for 50,000 cells in 50 μl/well in RPMI media with 2% FBS. Cells were plated using a multichannel pipette onto the compound dilutions in Greiner, 384 well, black clear bottom tissue culture treated plates (781090). The plates were incubated in 37° C. incubator at 5% $CO_2$ for 2 hours.

After the 2 hour incubation, the cell plates were spun in the centrifuge for 5 minutes at 1200 rpm. Using the Felix (CyBio), 8 μl of the supernatant was transferred to 384 well, low volume, white proxy plates. (Perkin Elmer, 6008230). A human IL1beta hTRF kit was used to analyze the supernatant (CISBIO, 62HIL1BPEG). The kit instructions were followed for preparing the IL1Beta standard curve and then the antibodies from the kit were diluted 1:40 rather than 1:20 as kit instructed. Once combined, the antibodies were added across the plates, 5 μl/well. The plates were sealed and incubated at 4° C. overnight. The plates were then read on the Perkin Elmer EnVision at 665/615 nm using the hTRF laser. Compounds exhibited a dose-related increase of IL-1β production.

Measurement of IL-1β Production—Human Whole Blood Assay

Serial dilutions of compounds in DMSO were added to low volume 384 well plates at 100 nl/well using an ECHO 550 acoustic dispenser (Labcyte) to achieve final starting concentration of 10 uM in assay.

Human venous whole blood obtained from healthy donors was pre-treated with LPS (Invivogen, Cat #tlrl-eblps) at 1 ng/ml for four hours at 37° C. in a humidified 95% air/5% CO2 incubator. Primed blood was added to the compound plate and incubated for additional 4 hours at 37° C. IL-1beta in the supernatants was measured using AlphLISA kit (Cat #AL220) according to manufacturer's instructions. Compounds exhibited a dose-related increase of IL-1β production. EC50 was determined using primed but untreated blood as baseline.

Measurement of IL-1β Production—Mouse hTRF Protocol

Immortalized mouse macrophages derived from $C_{57}BL/6$ mice were obtained from Ericke Latz, University of Bonn/University of Massachusetts Worchester, MA. The cells were harvested using 0.05% Trypsin and washed with PBS. Cell were plated at 30,000 cells per well in 25 ul in DMEM (Gibco, 11965) supplemented with 2% FBS and incubated for 10 minutes at 37° C. at 5% $CO_2$. LPS-EB (Invivogen, tlr-eblps) was added to a final concentration of 200 ng/ml at 5 ul/well and cells were incubated for 2 hours at 37° C. at 5% $CO_2$.

Serial dilutions of compounds in DMSO were added to cells in low volume 384 well plates at 60 nl/well using an ECHO 550 acoustic dispenser (Labcyte) to achieve final starting concentration of 50 uM in assay and incubated with compounds for additional 2 hours at 37° C. at 5% $CO_2$.

After the 2 hour incubation, the cell plates were spun in the centrifuge for 5 minutes at 1200 rpm. Using the Felix (CyBio), 8 ul of the supernatant was transferred to 384 well, low volume, white proxy plates. (Perkin Elmer, 6008230). A human IL1beta hTRF kit was used to analyze the supernatant (CISBIO, 62MIL1BPEH). The kit instructions were followed for preparing the IL1Beta standard curve (the antibodies from the kit were diluted 1:40 rather than 1:20 as kit instructed). Once combined, the antibodies were added across the plates at 5 ul/well. The plates were sealed and incubated at 4° C. overnight. The plates were read on the Perkin Elmer EnVision at 665/615 nm using the hTRF laser. Data was then converted to pg/ml of Il1Beta. Compounds exhibited a dose-related increase of IL-1β production.

In Vitro Human TLR7 and TLR8 Binding Reporter Assays

Logarithmically-growing human HEK-Blue cells co-expressing a TLR7 or TLR8 gene and a NF-kB/AP1-inducible SEAP (secreted embryonic alkaline phosphatase; Invivogen, San Diego, CA) reporter gene are added to individual wells of a 384-well plate (15,000 cells per 20 μL per well) and maintained for 24 h at 37° C., 5% $CO_2$. Test compounds or DMSO are distributed to separate wells the next day using acoustic liquid handling technology (100 nL per well) and cells are subsequently incubated for 18 h at 37° C., 5% $CO_2$. Cellular SEAP production is measured using an Envision plate reader instrument thirty minutes after adding freshly-made Quanti-Blue reagent (prepared by following manufacturer instructions; Invivogen, San Diego, CA) to the HEK-Blue TLR Nf-kB-SEAP cell reactions. All $EC_{50}$ values (half-maximal effective concentration) are determined using proprietary data analysis software. Normalized $EC_{50}$ value=absolute value determined by setting 100% Ymax using a reference standard RLU (relative light unit) values from cells treated with 50 μM of the reference standard.

EXAMPLES

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

Biological data of compounds that were assayed using one or more of the above procedures. Unless otherwise indicated, the TLR7 agonist $EC_{50}$ and TLR8 agonist $EC_{50}$ of the below compounds were measured at values>100 μM.

HPLC/M5 and Preparatory/Analytical HPLC Methods Employed in Characterization or Purification of Examples Analytical HPLC/MS was performed using the following methods:

Method A: Column: Waters)(Bridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

Method B: Column: Acquity UPLC BEH C18, 1.7 μm particles; Mobile Phase A: 99.95:0.05 water:TFA; Mobile Phase B: 99.95:0.05 acetonitrile:TFA; Temperature: 50° C.; Gradient: 2% B to 98% B over 1.00 min, then a 0.50 min hold at 98% B; Flow: 0.8 mL/min; Detection: MS and UV (254 nm).

Nuclear Magnetic Resonance (NMR) Spectroscopy

Chemical shifts are reported in parts per million (ppm) downfield from internal tetramethylsilane (TMS) or from the position of TMS inferred by the deuterated NMR solvent. Apparent multiplicities are reported as: singlet—s, doublet—d, triplet—t, quartet—q, or multiplet—m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities. In some cases, NMR spectra are obtained using water peak suppression, which may result in overlapping peaks not being visible or having altered shape and/or integration.

Example 1. 3-((2-amino-7-(1H-pyrazol-3-yl)-1,8-naphthyridin-4-yl)amino)propan-1-ol

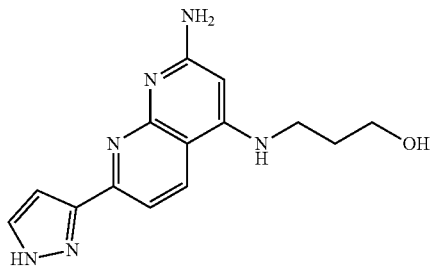 [SMILES: Nc1cc(NCCCO)c2ccc(-c3cc[nH]n3)nc2n1]

1A. Methyl 2-amino-6-bromonicotinate

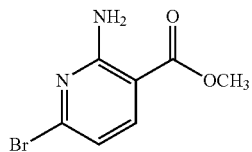 [SMILES: COC(=O)c1ccc(Br)nc1N]

To a solution of 2-amino-6-bromonicotinic acid (1.00 g, 4.61 mmol) in a mixture of dichloromethane (30 mL) and methanol (15 mL) cooled to 0° C. was added trimethylsilyldiazomethane (2 M in hexane, 2.76 mL, 5.53 mmol) slowly. Once the addition was complete, the ice bath was removed, and the reaction mixture was allowed to warm to room temperature and stirred for 30 min. Analysis indicated that starting material was still present. An additional 1.2 mL of the trimethylsilyldiazomethane (2 M in hexane) was added, and the reaction was stirred overnight. The reaction mixture was concentrated and dried well under reduced pressure to give methyl 2-amino-6-bromonicotinate as a pale yellow solid. LC/MS [M+H]$^+$=230.9 and 232.9.

1B. 3-(2-Amino-6-bromopyridin-3-yl)-3-oxopropanenitrile

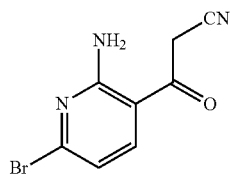 [SMILES: N#CCC(=O)c1ccc(Br)nc1N]

To a solution of acetonitrile (1.20 mL, 22.9 mmol) in tetrahydrofuran (12 mL), cooled to −78° C. with a dry-ice/acetone bath, was added n-butyl lithium (11M in hexane) (1.34 mL, 14.7 mmol). The mixture was stirred at −78° C. for 0.5 h. To the solution was added methyl 2-amino-6-bromonicotinate (1.06 g, 4.59 mmol) dissolved in tetrahydrofuran (12 mL). The resulting reaction mixture was stirred for 1 h at −78° C. Analysis indicated that there was still starting material remaining, so additional nBuLi (1.0 mL) was added. After 30 min., the reaction was quenched with a saturated aqueous solution of ammonium chloride, and the mixture was diluted with ethyl acetate, washed with a saturated aqueous solution of ammonium chloride, and washed with brine. The organic layer was collected, and the aqueous layers were sequentially extracted with ethyl acetate. The combined organic layers were dried over anhydrous sodium sulfate and concentrated under reduced pressure. Purification by ISCO silica gel chromatography (80 g column; 0-100% ethyl acetate in hexane) afforded 3-(2-amino-6-bromopyridin-3-yl)-3-oxopropanenitrile (0.672 g, 2.80 mmol, 61% yield) as a pale yellow solid. LC/MS [M+H]$^+$=240.0 and 242.0.

1C. 2-Amino-7-bromo-1,8-naphthyridin-4-ol

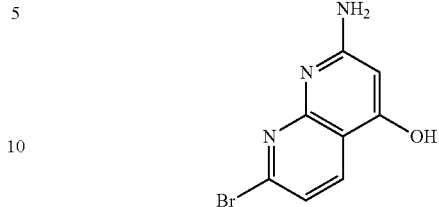

To a mixture of 3-(2-amino-6-bromopyridin-3-yl)-3-oxopropanenitrile (0.672 g, 2.80 mmol) in ethanol (15 mL) in a 30 mL sealed tube was added a solution of sodium ethoxide (21% wt in ethanol) (1.1 mL, 2.80 mmol). The homogeneous reaction mixture was sealed and heated at 100° C. overnight. The resulting precipitate was collected by vacuum filtration, washed with ethanol, and dried well to give 2-amino-7-bromo-1,8-naphthyridin-4-ol (0.479 g, 1.98 mmol, 71% yield) as an off-white solid. The filtrate contained additional product. LC/MS [M+1]$^+$=240.0 and 242.0.

1D. 2-Amino-7-(1-(tetrahydro-2H-pyran-2-yl)-1H-pyrazol-5-yl)-1,8-naphthyridin-4-ol

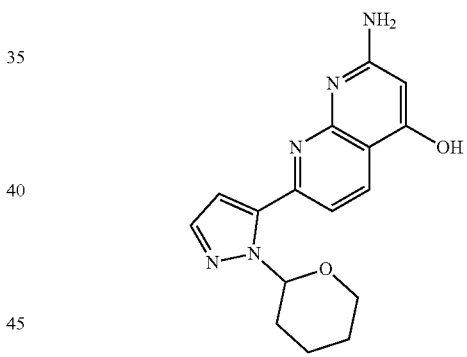

A mixture of 2-amino-7-bromo-1,8-naphthyridin-4-ol (0.479 g, 2.00 mmol), 1-(tetrahydro-2H-pyran-2-yl)-5-(4,4,5,5-tetramethyl-1,3,2-dioxaborolan-2-yl)-1H-pyrazole (1.110 g, 3.99 mmol), and potassium carbonate (2M in water, 2.99 mL, 5.99 mmol) in dioxane (12 mL) was degassed (3×; vacuum/nitrogen). To the mixture was added 1,1'-bis(diphenylphosphino)ferrocene-palladium(II)dichloride (0.146 g, 0.200 mmol), and the mixture degassed (3×; vacuum/nitrogen). The reaction was immersed in an oil bath at 100° C. and stirred 4 h. The reaction mixture was diluted with ethyl acetate and water, and the resulting precipitate was collected by vacuum filtration, washed with water, washed with ethyl acetate, and dried well to give 2-amino-7-(1-(tetrahydro-2H-pyran-2-yl)-1H-pyrazol-5-yl)-1,8-naphthyridin-4-ol (0.604 g, 1.92 mmol, 96% yield) as a light gray solid. LC/MS [M+H]$^+$=312.3.

1E. 4-Chloro-7-(1H-pyrazol-5-yl)-1,8-naphthyridin-2-amine

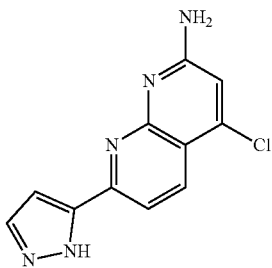 [SMILES: Nc1cc(Cl)c2ccc(-c3ccn[nH]3)nc2n1]

A mixture of 2-amino-7-(1-(tetrahydro-2H-pyran-2-yl)-1H-pyrazol-5-yl)-1,8-naphthyridin-4-ol (0.200 g, 0.642 mmol) and POCl₃ (2.036 ml, 21.84 mmol) was immersed in an oil bath at 100° C. and stirred overnight. The black reaction mixture was concentrated under reduced pressure, and the residue was pre-absorbed on silica gel and purified by ISCO silica gel chromatography (24 g column; 0-30% methanol in dichloromethane) to give 4-chloro-7-(1H-pyrazol-5-yl)-1,8-naphthyridin-2-amine (0.116 g, 0.472 mmol, 74% yield) as a yellow solid. LC/MS [M+H]⁺=246.1.

Example 1

A mixture of 4-chloro-7-(1H-pyrazol-3-yl)-1,8-naphthyridin-2-amine (0.023 g, 0.094 mmol), 3-aminopropan-1-ol (0.036 mL, 0.468 mmol), and Hunig's base (0.16 mL, 0.936 mmol) in N-methyl-2-pyrrolidinone (1.0 mL) in a sealed 2 dram vial was heated at 120° C. overnight. The crude material was purified by reverse-phase, preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-30% B over 20 minutes, then a 4-minute hold at 100% B; Flow Rate: 20 mL/min; Column Temperature: 25 C. Fractions containing the desired product were combined and dried via centrifugal evaporation to give 3-((2-amino-7-(1H-pyrazol-3-yl)-1,8-naphthyridin-4-yl)amino)propan-1-ol (12.4 mg).

Example 2. (1S,3S)-3-((2-amino-7-(1H-pyrazol-5-yl)-1,6-naphthyridin-4-yl)amino)cyclopentan-1-ol

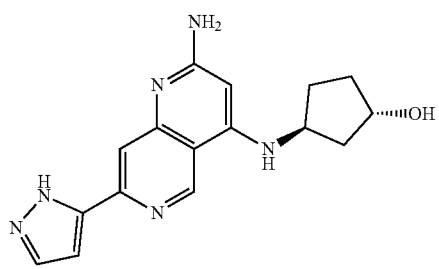 [SMILES: Nc1cc(N[C@H]2CC[C@H](O)C2)c2cnc(-c3ccn[nH]3)cc2n1]

2A. Methyl 4-amino-6-chloronicotinate

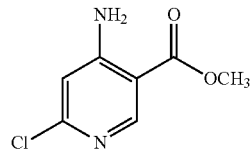 [SMILES: COC(=O)c1cnc(Cl)cc1N]

To a suspension of 4-amino-6-chloronicotinic acid (500 mg, 2.90 mmol) in dichloromethane (5 mL) and methanol (5 mL) was added TMS-diazomethane (2.90 mL, 5.79 mmol, 2.0 M in hexanes). The resulting mixture was stirred at room temperature for 2 h. The reaction was concentrated under reduced pressure, and the resulting grey solid was used in the next step without purification. LC/MS [M+H]⁺=187.0. ¹H-NMR (400 MHz, CHLOROFORM-d) δ 8.89 (s, 1H), 6.78 (s, 1H), and 3.97 (s, 3H).

2B. Methyl 4-amino-6-(1-(tetrahydro-2H-pyran-2-yl)-1H-pyrazol-5-yl)nicotinate

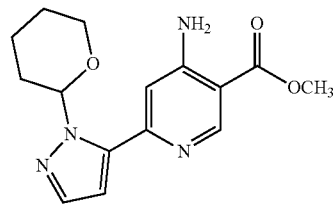 [SMILES: COC(=O)c1cnc(-c2ccnn2C2CCCCO2)cc1N]

To a solution of methyl 4-amino-6-chloronicotinate (110 mg, 0.590 mmol) in dioxane (10 mL) was added 1-(tetrahydro-2H-pyran-2-yl)-5-(4,4,5,5-tetramethyl-1,3,2-dioxaborolan-2-yl)-1H-pyrazole (180 mg, 0.648 mmol), and potassium phosphate, tribasic (0.590 mL, 1.18 mmol). Nitrogen was bubbled through the reaction mixture for 5 min., and then PdCl₂(dppf) (26 mg, 0.035 mmol) was added, followed by additional bubbling with (5 min.). The reaction vessel was sealed, and the reaction was stirred at 100° C. for 3 h. The reaction was filtered through a pad of Celite and concentrated. Purification by ISCO silica gel chromatography (40 g column, 50% EtOAc/hexanes) provided the methyl 4-amino-6-(1-(tetrahydro-2H-pyran-2-yl)-1H-pyrazol-5-yl)nicotinate (160 mg, 90% yield). LC/MS [M+H–THP]⁺=303.3; [M–THP+H]⁺=219.1.

2C. 3-(4-Amino-6-(1-(tetrahydro-2H-pyran-2-yl)-1H-pyrazol-5-yl)pyridin-3-yl)-3-oxopropanenitrile

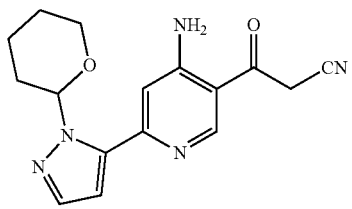 [SMILES: N#CCC(=O)c1cnc(-c2ccnn2C2CCCCO2)cc1N]

To a stirred solution of acetonitrile (0.216 mL, 4.13 mmol) in THF (10 mL) at −78° C. was added n-butyl lithium (0.38 mL, 4.13 mmol), 11.0M in hexanes). The resulting mixture was stirred at −78° C. for 1 h. A solution of methyl 4-amino-6-(1-(tetrahydro-2H-pyran-2-yl)-1H-pyrazol-5-yl)nicotinate (250 mg, 0.827 mmol) in 5 mL THF was added dropwise over 15 min. The reaction was stirred at −78° C. for 30 min. and warmed to room temperature. A saturated aqueous NH$_4$Cl solution was added, and the reaction mixture was extracted with EtOAc (3×). The combined organic layers were washed with saturated NH$_4$C$_1$, washed with water, dried (Na$_2$SO$_4$), and concentrated. Purification by ISCO silica gel chromatography (40 g column, 10%-50% EtOAc/hexanes) afforded 3-(4-amino-6-(1-(tetrahydro-2H-pyran-2-yl)-1H-pyrazol-5-yl)pyridin-3-yl)-3-oxopropanenitrile (200 mg, 78% yield). LC/MS [M+H]$^+$=312.2; [M−THP+H]$^+$=228.1.

2D. 2-Amino-7-(1-(tetrahydro-2H-pyran-2-yl)-1H-pyrazol-5-yl)-1,6-naphthyridin-4-ol

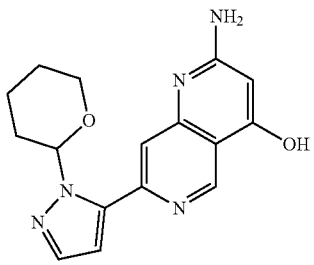 [SMILES: Nc1cc(O)c2cnc(-c3ccnn3C3CCCCO3)cc2n1]

A solution of 3-(4-amino-6-(1-(tetrahydro-2H-pyran-2-yl)-1H-pyrazol-5-yl)pyridin-3-yl)-3-oxopropanenitrile (110 mg, 0.353 mmol) in EtOH (3 mL) and sodium ethoxide (0.132 mL, 0.353 mmol) was heated at 100° C. for 12 h. Purification by reverse-phase, preparative HPLC provided 2-Amino-7-(1-(tetrahydro-2H-pyran-2-yl)-1H-pyrazol-5-yl)-1,6-naphthyridin-4-ol (80 mg, 73% yield). LC/MS [M+H]$^+$=312.2; [M−THP+H]$^+$=228.1.

2E. 4-Chloro-7-(1H-pyrazol-5-yl)-1,6-naphthyridin-2-amine

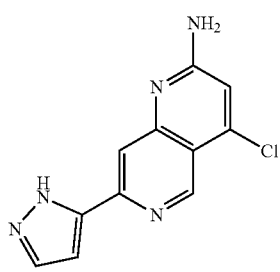 [SMILES: Nc1cc(Cl)c2cnc(-c3ccn[nH]3)cc2n1]

A solution of 2-amino-7-(1-(tetrahydro-2H-pyran-2-yl)-1H-pyrazol-5-yl)-1,6-naphthyridin-4-ol (60 mg, 0.193 mmol) and POCl$_3$ (0.5 mL, 5.36 mmol) was heated at 105° C. for 12 h. The reaction mixture was concentrated under reduced pressure to remove most of POCl$_3$, and then the residue was added to 2 mL ice-water. The resulting mixture was purified by reverse-phase, preparative HPLC to yield 4-chloro-7-(1H-pyrazol-5-yl)-1,6-naphthyridin-2-amine (30 mg, 63.4% yield) as a white solid. LC/MS [M+H]$^+$=246.0. $^1$H-NMR (400 MHz, METHANOL-d$_4$) δ 9.19-9.11 (m, 1H), 8.11-8.03 (m, 1H), 7.91-7.84 (m, 1H), 7.26-7.20 (m, 1H), and 7.15-7.07 (m, 1H).

Example 2

A solution of 4-chloro-7-(1H-pyrazol-5-yl)-1,6-naphthyridin-2-amine (8 mg, 0.033 mmol), NMP (1 mL), and DIEA (0.057 mL, 0.326 mmol) was heated at 160° C. for 15 h. Purification by reverse-phase, preparative HPLC yielded (1S,3S)-3-((2-amino-7-(1H-pyrazol-5-yl)-1,6-naphthyridin-4-yl)amino)cyclopentan-1-ol (6 mg, 54% yield).

Example 3. 2-((2-amino-7-(1H-pyrazol-3-yl)-1,5-naphthyridin-4-yl)amino)ethan-1-ol

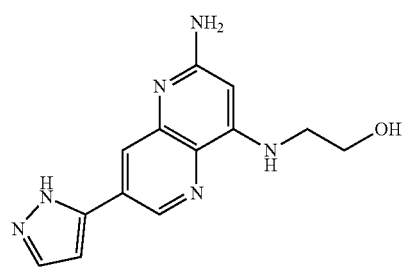 [SMILES: Nc1cc(NCCO)c2ncc(-c3ccn[nH]3)cc2n1]

3A. 5-((5-Bromopyridin-3-yl)amino)methylene)-2,2-dimethyl-1,3-dioxane-4,6-dione

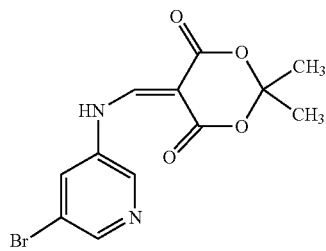 [SMILES: CC1(C)OC(=O)C(=CNc2cncc(Br)c2)C(=O)O1]

A mixture of Meldrum's acid, 2,2-dimethyl-1,3-dioxane-4,6-dione (7.21 g, 50.0 mmol), and triethoxymethane (7.98 ml, 48.0 mmol) was heated at 90° C. for 1 h. The resulting dark solution was cooled to 70° C. and treated with 5-bromopyridin-3-amine (6.92 g, 40.0 mmol) over 10 min. (EtOH chase). This mixture was stirred 30 min. at 70° C. then cooled to room temperature, filtered (EtOH then Et$_2$O rinses), and dried to afford 5-(((5-bromopyridin-3-yl)amino)methylene)-2,2-dimethyl-1,3-dioxane-4,6-dione (9.8 g, 75% yield) as a yellow powder. LC/MS [M+H]$^+$=328.3. $^1$H-NMR (400 MHz, CHLOROFORM-d) δ 8.64-8.58 (m, 2H), 8.56-8.52 (m, 1H), 7.89-7.74 (m, 1H), 7.34-7.17 (m, 1H), and 1.87-1.72 (m, 6H).

3B. 7-Bromo-1,5-naphthyridin-4-ol

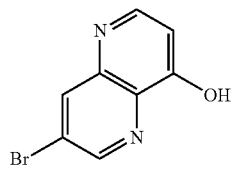 [SMILES: Oc1ccnc2cc(Br)cnc12]

To a DowThermA (100 mL), heated at 240° C., was added in small portions over 5 min. 5-(((5-bromopyridin-3-yl)amino)methylene)-2,2-dimethyl-1,3-dioxane-4,6-dione (10 g, 30.6 mmol). With each portion, vigorous bubbling was observed (presumably as decarboxylation occurred). Halfway through the addition, the product began to precipitate. After the addition was complete, heating was continued for 5 min. and then for an additional 1 h as it cooled to 45° C. The precipitate was collected by vacuum filtration, rinsed with hexanes, and air-dried to afford a brown powder. This material was suspended in 150 mL of a 9:1 mixture of EtOH and water and brought to reflux. The mixture was filtered hot and rinsed with EtOH. The solid was dried to afford 7-bromo-1,5-naphthyridin-4-ol (4.8 g, 70% yield) as a brown solid. LC/MS $[M+H]^+$=224.8.

3C. 3-Bromo-8-chloro-1,5-naphthyridine

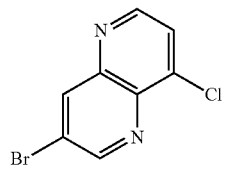 [SMILES: Clc1ccnc2cc(Br)cnc12]

A mixture of 7-bromo-1,5-naphthyridin-4-ol (2 g, 8.89 mmol) and $POCl_3$ (10 mL, 107 mmol) was heated at 105° C. for 1 h. The reaction mixture was cooled and transferred by pipette to stirred ice water. The pH was adjusted to ~5 with sat. aqueous sodium bicarbonate, and the resulting precipitate was filtered, rinsed with water, and dried to afford the 3-Bromo-8-chloro-1,5-naphthyridine (1.2 g, 50% yield) as a solid. LC/MS $[M+H]^+$=244.0. $^1$H-NMR (400 MHz, CHLOROFORM-d) δ 9.13-9.05 (m, 1H), 8.90-8.83 (m, 1H), 8.69-8.60 (m, 1H), and 7.81-7.75 (m, 1H).

3D. 7-Bromo-4-chloro-1,5-naphthyridine 1-oxide

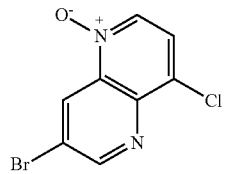

A solution of 3-bromo-8-chloro-1,5-naphthyridine (150 mg, 0.616 mmol) in dichloromethane (3 mL) was treated with m-CPBA (207 mg, 0.924 mmol) 1.02 mmol) and stirred at room temperature for 10 min. The reaction mixture was diluted with EtOAc (10 mL), washed twice with diluted aqueous $K_2CO_3$, and the organic layer was dried over anhydrous sodium sulfate and concentrated to afford 7-bromo-4-chloro-1,5-naphthyridine 1-oxide (120 mg, 68% yield) as a white solid. LC/MS $[M+H]^+$=244.0. $^1$H-NMR (400 MHz, CHLOROFORM-d) δ 9.30-9.24 (m, 1H), 9.19-9.11 (m, 1H), 8.52-8.43 (m, 1H), and 7.69-7.62 (m, 1H).

3E. 7-Bromo-4-chloro-1,5-naphthyridine

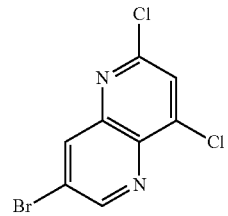 [SMILES: Clc1cc(Cl)c2ncc(Br)cc2n1]

A solution of 7-bromo-4-chloro-1,5-naphthyridine 1-oxide (112 mg, 0.432 mmol) in $POCl_3$ (1 mL, 10.73 mmol) was heated at 90° C. with stirring for 1 h. The reaction was concentrated under reduced pressure and then added to ice water. The aqueous mixture was extracted with dichloromethane (3×), and the combined organic layers were dried over anhydrous sodium sulfate, and concentrated. The crude material was used directly in next step without purification. LC/MS $[M+H]^+$=279.0.

3F. 2-((7-Bromo-2-chloro-1,5-naphthyridin-4-yl)amino)ethan-1-ol

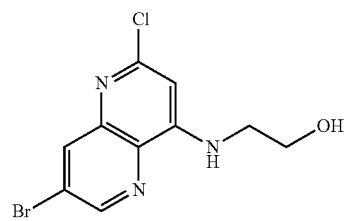 [SMILES: OCCNc1cc(Cl)nc2cc(Br)cnc12]

A solution of 7-bromo-2,4-dichloro-1,5-naphthyridine (161 mg, 0.578 mmol) and 2-aminoethan-1-ol (0.5 mL, 0.578 mmol) in NMP (2 mL) was stirred at 120° C. After 2 hours, the reaction mixture was partitioned between EtOAc and water. The organic layer was collected, and the aqueous layer was with EtOAc. The combined organic layers were dried over sodium sulfate, filtered, and concentrated to give a brownish sticky oil. Purification by reverse-phase, preparative HPLC provided 2-((7-bromo-2-chloro-1,5-naphthyridin-4-yl)amino)ethan-1-ol (60 mg, 31% yield) as a light yellow solid. LC/MS $[M+H]^+$=303.9.

3G. 2-((2-Chloro-7-(1H-pyrazol-3-yl)-1,5-naphthyridin-4-yl)amino)ethan-1-ol

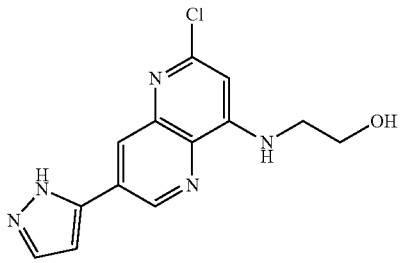 [SMILES: OCCNc1cc(Cl)nc2cc(-c3ccn[nH]3)cnc12]

To a solution of 2-((7-bromo-2-chloro-1,5-naphthyridin-4-yl)amino)ethan-1-ol (20 mg, 0.066 mmol) in 1,4-dioxane (2 mL) was added 3-(4,4,5,5-tetramethyl-1,3,2-dioxaborolan-2-yl)-1H-pyrazole (15.39 mg, 0.079 mmol) and potassium phosphate, dibasic (0.099 mL, 0.198 mmol). The mixture was degassed by bubbling nitrogen through for 5 min, and then bis(tri-tert-butylphosphine)palladium(O) (3.38 mg, 6.61 μmol) was added, with additional nitrogen bubbling (5 min.). The reaction vessel was sealed, and the reaction was heated at 80° C. for 3 h. The crude reaction mixture was purified by reverse-phase, preparative HPLC to yield 2-((2-chloro-7-(1H-pyrazol-3-yl)-1,5-naphthyridin-4-yl)amino)ethan-1-ol (10 mg, 52% yield). LC/MS [M+H]$^+$ =289.8. $^1$H-NMR (400 MHz, METHANOL-$d_4$) δ 9.41-9.29 (m, 1H), 8.45-8.35 (m, 1H), 7.89-7.79 (m, 1H), 7.09-6.92 (m, 2H), 3.95-3.86 (m, 2H), 3.72-3.64 (m, 2H).

Example 3

To a solution of 2-((2-chloro-7-(1H-pyrazol-3-yl)-1,5-naphthyridin-4-yl)amino)ethan-1-ol (15 mg, 0.052 mmol) in NMP (1 mL) was added 4-methoxybenzylamine (0.034 mL, 0.259 mmol). The resulted mixture was heated at 150° C. for 3 h. Purification by reverse-phase, preparative HPLC afforded 2-((2-((4-methoxybenzyl)amino)-7-(1H-pyrazol-3-yl)-1,5-naphthyridin-4-yl)amino)ethan-1-ol. The PMB group was removed in neat TFA (1 mL) upon heating at 80° C. for 3 h. Purification of the crude product by reverse-phase, preparative HPLC afforded 2-((2-amino-7-(1H-pyrazol-3-yl)-1,5-naphthyridin-4-yl)amino)ethan-1-ol (1.3 mg, 9.3% yield).

Example 4. (1S,3S)-3-((2-amino-7-(1H-pyrazol-5-yl)-1,5-naphthyridin-4-yl)amino)cyclopentan-1-ol

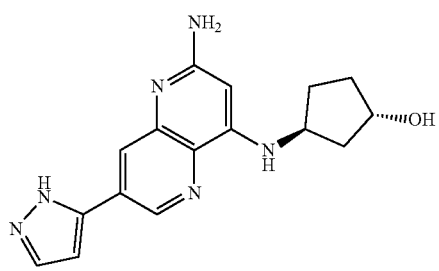 [SMILES: Nc1cc(N[C@H]2CC[C@H](O)C2)c2ncc(-c3ccn[nH]3)cc2n1]

4A. 3-(3-Amino-5-bromopyridin-2-yl)-3-oxopropanenitrile

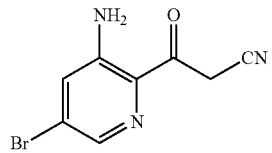 [SMILES: N#CCC(=O)c1ncc(Br)cc1N]

To a stirred solution of acetonitrile (1.13 mL, 21.6 mmol) in THF (20 mL) at −78° C. was added n-butyl lithium (1.97 mL, 21.6 mmol), 11.0 M in hexanes). The resulting mixture was stirred at −78° C. for 1 h. Methyl 3-amino-5-bromopicolinate (500 mg, 2.16 mmol) in 10 mL THF was added dropwise over 15 min., and the reaction was stirred at −78° C. for 30 min. and then warmed to room temperature. A saturated NH$_4$C$_1$ solution was added, and the reaction mixture was extracted with EtOAc (3×). The combined organic layer was washed with saturated NH$_4$C$_1$ and water, dried (Na$_2$SO$_4$), and concentrated. Purification by ISCO silica gel chromatography (40 g column, 10%-50% EtOAc/hexanes) afforded 3-(3-amino-5-bromopyridin-2-yl)-3-oxopropanenitrile (500 mg, 96% yield). LC/MS [M+1]$^+$=240.1. $^1$HNMR (400 MHz, METHANOL-$d_4$) δ 7.99-7.85 (m, 1H), 7.56-7.34 (m, 1H), and 4.57-4.37 (m, 2H).

4B. 2-Amino-7-bromo-1,5-naphthyridin-4-ol

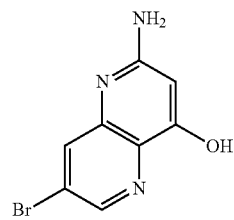 [SMILES: Nc1cc(O)c2ncc(Br)cc2n1]

A solution of 3-(3-amino-5-bromopyridin-2-yl)-3-oxopropanenitrile (200 mg, 0.833 mmol) and sodium ethoxide (0.261 mL, 0.833 mmol) in EtOH (20 mL) was heated at 100° C. for 12 h. The ethanol was removed under reduced pressure, and the residue was purified by reverse-phase, preparative HPLC to yield 2-amino-7-bromo-1,5-naphthyridin-4-ol (160 mg, 80% yield). LC/MS [M+1]$^+$=241.9. $^1$H-NMR (400 MHz, METHANOL-$d_4$) δ 8.84-8.75 (m, 1H), 8.29-8.19 (m, 1H), and 6.54-6.40 (m, 1H).

4C. 7-Bromo-4-chloro-1,5-naphthyridin-2-amine

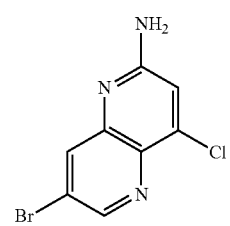 [SMILES: Nc1cc(Cl)c2ncc(Br)cc2n1]

A solution of 2-amino-7-bromo-1,5-naphthyridin-4-ol (10 mg, 0.042 mmol) in POCl₃ (1 mL, 10.73 mmol) was heated at 100° C. overnight. The reaction mixture was concentrated under reduced pressure, and purified by reverse-phase, preparative HPLC to yield the desired product 7-bromo-4-chloro-1,5-naphthyridin-2-amine (10 mg, 93% yield) as a light pink colored solid. LC/MS [H+M]$^+$=258.0. $^1$H-NMR (400 MHz, METHANOL-d₄) δ 8.78-8.66 (m, 1H), 8.26-8.16 (m, 1H), and 7.36-7.27 (m, 1H).

4D. (1S,3S)-3-((2-Amino-7-bromo-1,5-naphthyridin-4-yl)amino)cyclopentan-1-ol

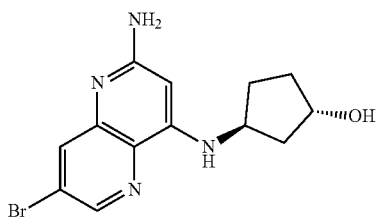 [SMILES: Nc1cc(N[C@H]2CC[C@H](O)C2)c2ncc(Br)cc2n1]

A solution of 7-bromo-4-chloro-1,5-naphthyridin-2-amine (10 mg, 0.039 mmol) and (1S,3S)-3-aminocyclopentan-1-ol (11.74 mg, 0.116 mmol) in NMP (1 mL) and DIEA (0.034 mL, 0.193 mmol) was heated at 150° C. for 12 h. The reaction mixture was concentrated and purified by reverse phase, preparative HPLC to yield the desired product (8 mg, 64% yield) as a white solid. LC/MS [M+H]$^+$=324.0.

Example 4

A solution of (1S,3S)-3-((2-amino-7-bromo-1,5-naphthyridin-4-yl)amino)cyclopentan-1-ol (8 mg, 0.025 mmol) in 1,4-dioxane (2 mL) was added 5-(4,4,5,5-tetramethyl-1,3,2-dioxaborolan-2-yl)-1H-pyrazole (5.8 mg, 0.030 mmol), potassium phosphate, tribasic (0.037 mL, 0.074 mmol) (2M in water) was purged by bubbling nitrogen for 5 min. PdCl₂(dppf)-CH₂Cl₂ adduct (2.0 mg, 2.475 µmol) was added, with additional purging, and the reaction vessel was sealed and stirred at 100° C. for 12 h. Purification by reverse-phase, preparative HPLC afforded (1S,3S)-3-((2-amino-7-(1H-pyrazol-5-yl)-1,5-naphthyridin-4-yl)amino)cyclopentan-1-ol (3.5 mg, 46% yield).

Example 5. 4-(1H-pyrazol-3-yl)-7-(1H-pyrazol-5-yl)-1,5-naphthyridin-2-amine

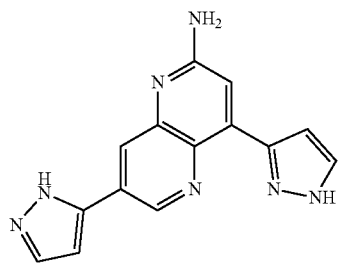 [SMILES: Nc1cc(-c2cc[nH]n2)c2ncc(-c3ccn[nH]3)cc2n1]

5A. 4-(1-(Tetrahydro-2H-pyran-2-yl)-1H-pyrazol-3-yl)-7-(1-tetrahydro-2H-pyran-2-yl)-1H-pyrazol-5-yl)-1,5-naphthyridin-2-amine

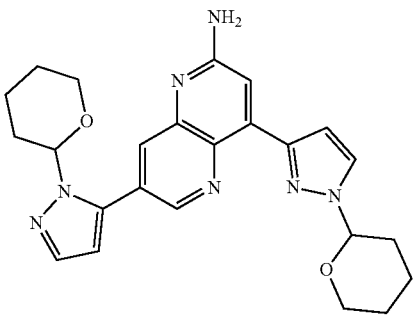 [SMILES: Nc1cc(-c2ccn(C3CCCCO3)n2)c2ncc(-c3ccnn3C3CCCCO3)cc2n1]

A solution of 7-bromo-4-chloro-1,5-naphthyridin-2-amine (0.026 g, 0.101 mmol) in dioxane (3.35 mL) was purged with nitrogen/vacuum (3×). To this solution was added potassium phosphate, tribasic (0.151 ml, 0.302 mmol, 2M in water), 1-(tetrahydro-2H-pyran-2-yl)-5-(4,4,5,5-tetramethyl-1,3,2-dioxaborolan-2-yl)-1H-pyrazole (0.034 g, 0.121 mmol), and [1,1'-bis(diphyenylphosphino)ferrocene] dichloropalladium(II) (3.7 mg, 5.03 µmol). The resulting solution was purged with nitrogen/vacuum and then stirred at 100° C. for 5 h. The reaction mixture was filtered, diluted with MeOH, and purified by reverse-phase, preparative HPLC to afford 4-(1-(tetrahydro-2H-pyran-2-yl)-1H-pyrazol-3-yl)-7-(1-tetrahydro-2H-pyran-2-yl)-1H-pyrazol-5-yl)-1,5-naphthyridin-2-amine (9.0 mg, 20% yield) as a light yellow solid. LC/MS m [M+H]$^+$=446.2.

Example 5

A solution of 4-(1-(tetrahydro-2H-pyran-2-yl)-1H-pyrazol-3-yl)-7-(1-(tetrahydro-2H-pyran-2-yl)-1H-pyrazol-5-yl)-1,5-naphthyridin-2-amine (9.0 mg, 0.020 mmol) in neat TFA (1 mL, 13.0 mmol) was stirred at 50° C. for 2 h. The TFA was removed reduced pressure, and the crude was dissolved in DMF, filtered, and purified by reverse-phase, preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-minute hold at 0% B, 0-30% B over 20 minutes, then a 4-minute hold at 100% B; Flow Rate: 20 mL/min to afford 4-(1H-pyrazol-3-yl)-7-(1H-pyrazol-5-yl)-1,5-naphthyridin-2-amine (4.5 mg, 57% yield).

Example 6. (R)-7-(1H-pyrazol-3-yl)-N4-(tetrahydro-furan-3-yl)pyrido[3,2-d]pyrimidine-2,4-diamine

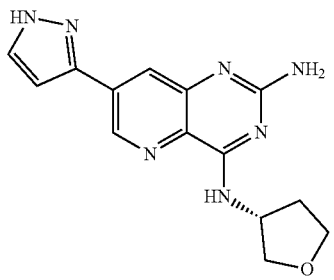 [SMILES: Nc1nc(N[C@@H]2CCOC2)c2ncc(-c3cc[nH]n3)cc2n1]

6A. 2-Amino-7-bromopyrido[3,2-d]pyrimidin-4(3H)-one

Guanidine hydrochloride (612 mg, 6.41 mmol) was suspended in DMA (10.7 mL) at room temperature. Sodium hydride (282 mg, 7.05 mmol) was added, and the reaction was stirred under $N_2$ for 1 h. Methyl 5-bromo-3-fluoropicolinate (500 mg, 2.137 mmol) was added in one portion, and the reaction was slowly heated to 160° C. for 1 h. After cooling to room temperature, ice-cold 5% aqueous citric acid solution (50 mL) was added to the reaction mixture to precipitate the product. 2-Amino-7-bromopyrido[3,2-d]pyrimidin-4(3H)-one was collected by vacuum filtration and dried overnight (528 mg). LC/MS $[M+H]^+=241/243$. $^1$H-NMR (400 MHz, DMSO-$d_6$) δ 11.30 (br d, J=0.7 Hz, 1H), 8.42 (d, J=2.0 Hz, 1H), 7.82 (d, J=2.0 Hz, 1H), and 6.72 (br s, 2H).

6B. (R)-7-Bromo-N4-(tetrahydrofuran-3-yl)pyrido[3,2-d]pyrimidine-2,4-diamine

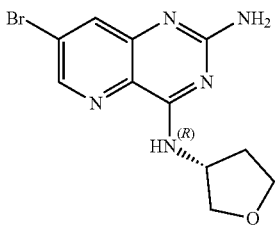

2-Amino-7-bromopyrido[3,2-d]pyrimidin-4(3H)-one (30 mg, 0.124 mmol) was suspended in DMF (622 μL) at room temperature. (R)-Tetrahydrofuran-3-amine (32.5 mg, 0.373 mmol) was added followed by DBU (28 μL, 0.187 mmol) and BOP (72 mg, 0.162 mmol). The reaction mixture was stirred overnight at room temperature. The reaction mixture was partitioned between EtOAc and $H_2O$. The aqueous phase was extracted with EtOAc (3×). The combined organic layers were dried over $Na_2SO_4$ and concentrated to afford (R)-7-bromo-N4-(tetrahydrofuran-3-yl)pyrido[3,2-d]pyrimidine-2,4-diamine (40.7 mg, 52% yield). LC/MS $[M+H]^+=310/312$.

Example 6

In a 2-dram reaction vial, (R)-7-bromo-N4-(tetrahydrofuran-3-yl)pyrido[3,2-d]pyrimidine-2,4-diamine (38 mg, 0.123 mmol) and 3-(4,4,5,5-tetramethyl-1,3,2-dioxaborolan-2-yl)-1H-pyrazole (28.5 mg, 0.147 mmol) were suspended in dioxane (1.2 mL) at room temperature. Aqueous tripotassium phosphate solution (2M, 184 μL, 0.368 mmol) was added, and $N_2$ was bubbled through the reaction mixture for 2 minutes. $PdCl_2$(dppf)-$CH_2Cl_2$ adduct (10.0 mg, 0.012 mmol) was introduced, and the reaction was purged with $N_2$ for another minute before sealing and heating to 100° C. for 90 minutes. After cooling to room temperature, the reaction mixture was diluted with EtOAc, filtered through a PTFE frit, and concentrated. The residue was redissolved in DMF and purified by reverse-phase, preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 22 minutes, then a 4-minute hold at 100% B; Flow Rate: 20 mL/min; Column Temperature: 25. Fractions containing the desired product were combined and dried via centrifugal evaporation to give (R)-7-(1H-pyrazol-3-yl)-N4-(tetrahydrofuran-3-yl)pyrido[3,2-d]pyrimidine-2,4-diamine (3.7 mg, 9.8% yield).

Example 7. (1S,3 S)-3-((2-amino-7-(1H-pyrazol-5-yl)pyrido[2,3-d]pyrimidin-4-yl)amino)cyclopentan-1-ol

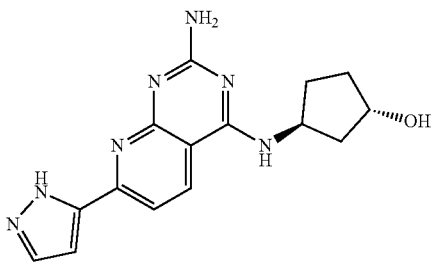 [SMILES: Nc1nc(N[C@H]2CC[C@H](O)C2)c2ccc(-c3ccn[nH]3)nc2n1]

7A. 2-Amino-7-chloropyrido[2,3-d]pyrimidin-4-ol

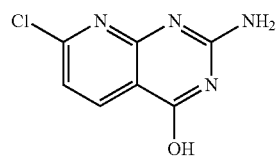 [SMILES: Nc1nc(O)c2ccc(Cl)nc2n1]

To a suspension of methyl 2,6-dichloronicotinate (1.0 g, 4.85 mmol) and guanidine hydrochloride (2.32 g, 24.3 mmol) in 2-propanol (32 mL) was added sodium tert-butoxide (2.33 g, 24.3 mmol). The reaction was heated to 90 C. After 6.5 hours, the reaction was concentrated. The residue was suspended in water, and the solid was removed by filtration. The pH of the aqueous layer was adjusted to approximately 5 with 1M HCl and a saturated bicarbonate solution. The solid was collected by vacuum filtration, rinsed with water, and dried to give 2-amino-7-chloropyrido[2,3-d]pyrimidin-4-ol (0.375 g, 1.907 mmol, 39% yield). $^1$H NMR (400 MHz, DMSO-$d_6$) δ 11.52-11.40 (m, 1H), 8.19 (d, J=8.1 Hz, 1H), 7.12 (d, J=8.1 Hz, 1H), and 7.05-6.96 (m, 2H).

7B. 2-Amino-7-(1-(tetrahydro-2H-pyran-2-yl)-1H-pyrazol-5-yl)pyrido[2,3-d]pyrimidin-4-ol

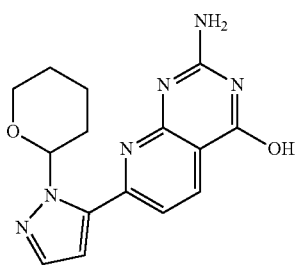 [SMILES: Nc1nc(O)c2ccc(-c3ccnn3C3CCCCO3)nc2n1]

A mixture of 1-(tetrahydro-2H-pyran-2-yl)-5-(4,4,5,5-tetramethyl-1,3,2-dioxaborolan-2-yl)-1H-pyrazole (184 mg, 0.661 mmol), 2-amino-7-chloropyrido[2,3-d]pyrimidin-4-ol (100 mg, 0.509 mmol), PdCl$_2$(dppf)-CH$_2$Cl$_2$ adduct (42 mg, 0.051 mmol), and K$_2$CO$_3$ (211 mg, 1.53 mmol) were placed in a pressure vial. The vial was placed under vacuum and backfilled with nitrogen three times. Dioxane (1.9 mL) and water (0.64 mL) were added, nitrogen was bubbled through the solution, and the reaction was then heated to 110° C. The reaction was cooled, diluted with water (pH is ~11), and filtered. The solid was rinsed with MeOH and EtOAc and then dried under reduced pressure. The filtrate was acidified to pH 7 with 1M HCl, and the resulting precipitate was collected by vacuum filtration to give 2-Amino-7-(1-(tetrahydro-2H-pyran-2-yl)-1H-pyrazol-5-yl)pyrido[2,3-d]pyrimidin-4-ol (88 mg, 55% yield). LC/MS [M+H−THP]$^+$=229.0.

Example 7

To a suspension of 2-amino-7-(1-(tetrahydro-2H-pyran-2-yl)-1H-pyrazol-5-yl)pyrido[2,3-d]pyrimidin-4-ol (36 mg, 0.115 mmol) and (1S,3S)-3-aminocyclopentan-1-ol, HCl (39.7 mg, 0.288 mmol) in DMF (0.8 mL) was added DBU (0.069 mL, 0.461 mmol) and BOP (66 mg, 0.150 mmol). After approximately 1 h, the reaction was diluted with water and extracted three times with EtOAc. The organic layers were concentrated, and the residue was dissolved in 0.5 mL DCM and 0.5 mL TFA. After approximately 1 h, the reaction was concentrated, azeotroped with DCM, dissolved in DMF, filtered through a syringe filter, and purified by reverse-phase, preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 25 minutes, then a 4-minute hold at 100% B; Flow Rate: 20 mL/min; Column Temperature: 25 C. Fractions containing the desired product were combined and dried via centrifugal evaporation to give (1S,3S)-3-((2-amino-7-(1H-pyrazol-5-yl)pyrido[2,3-d]pyrimidin-4-yl)amino)cyclopentan-1-ol, TFA (1.1 mg).

Starting with the appropriate starting material, Examples 8 through 10 were prepared in a similar fashion as described in the procedures for Example 1; Examples 11 through 12 were prepared in a similar fashion as described in the procedures for Example 2; Examples 13 through 14 were prepared in a similar fashion as described in the procedures for Example 3; Examples 15 through 16 and 23 through 29 were prepared in a similar fashion as described in the procedures for Example 4; Examples 17 through 21 and 30 through 31 were prepared in a similar fashion as described in the procedures for Example 6; and Example 22 was prepared in a similar fashion as described in the procedures for Example 7.

Biological data of compounds that were assayed using one or more of the above procedures. Unless otherwise indicated, the TLR7 agonist EC$_{50}$ and TLR8 agonist EC$_{50}$ of the below compounds were measured at values>100 μM.

| Ex. No. | Structure | LC/MS [M + H]$^+$/ RT(Method)/ NLRP3 hIL1β EC50 | $^1$H NMR (500 MHz, DMSO-$d_6$, unless otherwise indicated) |
|---|---|---|---|
| 1 | 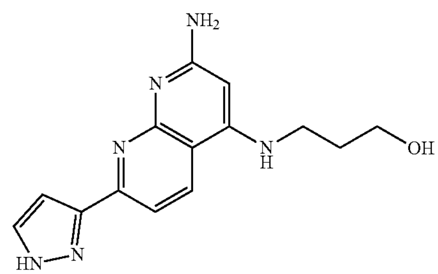 [SMILES: Nc1cc(NCCCO)c2ccc(-c3cc[nH]n3)nc2n1] | 285.0/ 0.96 min (A)/ 1.0 μM | δ 8.38 (d, J = 8.5 Hz, 1H), 7.82-7.69 (m, 1H), 7.68-7.56 (m, 1H), 6.95-6.83 (m, 2H), 6.33-6.21 (m, 2H), 5.79-5.69 (m, 1H). 3.56 (t, J = 6.3 Hz, 2H), 3.32-3.21 (m, 2H), and 1.84 (quin, J = 6.6 Hz, 2H). |

-continued

| Ex. No. | Structure | LC/MS [M + H]+/ RT(Method)/ NLRP3 hIL1β EC50 | 1H NMR (500 MHz, DMSO-d6, unless otherwise indicated) |
|---|---|---|---|
| 2 | 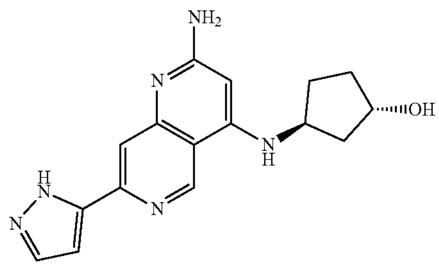 [SMILES: Nc1cc(N[C@H]2CC[C@H](O)C2)c2cnc(-c3ccn[nH]3)cc2n1] | 271.3/ 0.47 min (B)/ 17 μM | (400 MHz, METHANOL-d4) δ 9.46-9.36 (m, 1H), 8.09-8.01 (m, 1H), 7.96-7.90 (m, 1H), 7.83-7.75 (m, 1H), 7.26-7.18 (m, 1H), 2.47-2.43 (m, 2H), 2.12-2.09 (m, 2H), 1.83-1.79 (m, 2H), and 1.25-1.21 (m, 1H). |
| 3 | 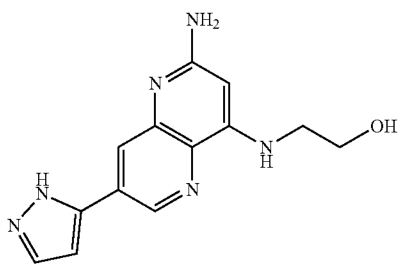 [SMILES: Nc1cc(NCCO)c2ncc(-c3ccn[nH]3)cc2n1] | 271.3/ 0.49 min (B)/ 0.31 μM | (400 MHz, METHANOL-d4) δ 9.17-9.09 (m, 1H), 8.25-8.18 (m, 1H), 7.87-7.81 (m, 1H), 7.00-6.91 (m, 1H), 6.05-5.99 (m, 1H), 3.94-3.84 (m, 2H), 3.61-3.53 (m, 2H). |
| 4 | 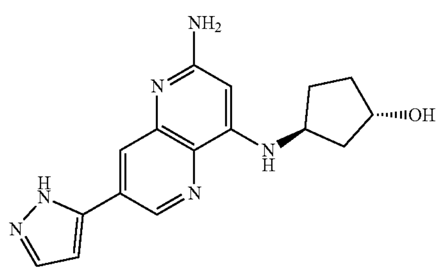 [SMILES: Nc1cc(N[C@H]2CC[C@H](O)C2)c2ncc(-c3ccn[nH]3)cc2n1] | 311.2/ 0.55 min (A)/ 3.5 μM | (400 MHz, METHANOL-d4) δ 9.17-9.09 (m, 1H), 8.28-8.19 (m, 1H), 7.86-7.79 (m, 1H), 6.99-6.91 (m, 1H), 6.02-5.97 (m, 1H), 5.62-5.57 (m, 1H), 4.51-4.42 (m, 1H), 4.33-4.20 (m, 1H), 2.53-2.38 (m, 1H), 2.29-2.10 (m, 2H), 1.85-1.71 (m, 2H). |
| 5 | 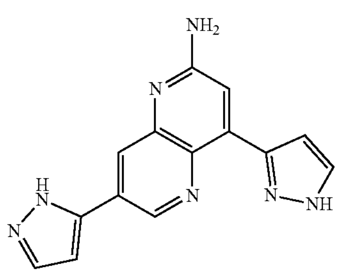 [SMILES: Nc1cc(-c2cc[nH]n2)c2ncc(-c3ccn[nH]3)cc2n1] | 278.0/ 1.08 min (A)/ 0.86 μM | δ 9.31-9.22 (m, 1H), 8.37 (d, J = 1.2 Hz, 1H), 7.97-7.85 (m, 2H), 7.83-7.69 (m, 1H), 7.63-7.44 (m, 1H), 7.02 (d, J = 2.1 Hz, 1H), 3.21-2.11 (m, 3H) |
| 6 | 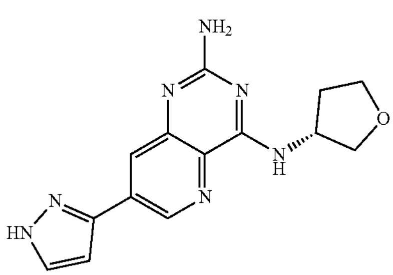 [SMILES: Nc1nc(N[C@@H]2CCOC2)c2ncc(-c3cc[nH]n3)cc2n1] | 298.1/ 0.85 min (A)/ 3.6 μM | δ 8.81 (br s, 1H), 7.93 (br d, J = 6.7 Hz, 1H), 7.90 (s, 1H), 7.86-7.73 (m, 1H), 6.94 (d, J = 1.8 Hz, 1H), 6.38 (br s, 2H), 4.74-4.61 (m, 1H), 4.00-3.87 (m, 2H), 3.80-3.72 (m, 1H), 3.67 (dd, J = 8.9, 5.2 Hz, 1H), 2.29-2.18 (m, 1H), 2.09 (dq, J = 12.6, 6.4 Hz, 1H); LC RT: 0.85 min. M/Z = 298.14. |

-continued

| Ex. No. | Structure | LC/MS [M + H]+/ RT(Method)/ NLRP3 hIL1β EC50 | 1H NMR (500 MHz, DMSO-d6, unless otherwise indicated) |
|---|---|---|---|
| 7 | 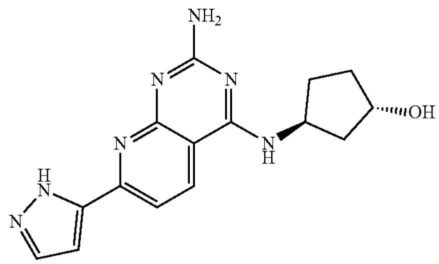 [SMILES: Nc1nc(N[C@H]2CC[C@H](O)C2)c2ccc(-c3ccn[nH]3)nc2n1] | 312.1/ 0.91 min (A)/ 5.7 μM | δ 9.20 (br d, J = 5.2 Hz, 1H), 8.75 (br d, J = 8.5 Hz, 1H), 8.00 (br d, J = 8.2 Hz, 1H), 7.91 (br s, 1H), 6.93 (br s, 1H), 4.92-4.81 (m, 1H), 4.29 (br s, 1H), 2.24-2.14 (m, 1H), 2.05-1.93 (m, 2H), 1.89-1.80 (m, 1H), and 1.67-1.48 (m, 2H) |
| 8 | 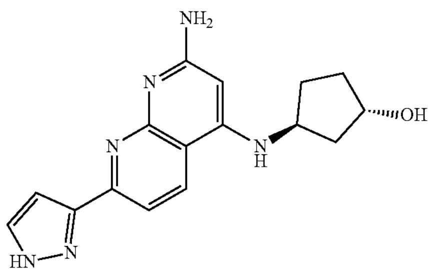 [SMILES: Nc1cc(N[C@H]2CC[C@H](O)C2)c2ccc(-c3cc[nH]n3)nc2n1] | 311.1/ 0.78 min (A)/ 1.6 μM | (500 MHz, DMSO-d6) δ 8.52-8.44 (m, 1H), 7.79-7.71 (m, 1H), 7.69-7.61 (m, 1H), 6.96-6.89 (m, 1H), 6.82-6.75 (m, 1H), 6.57-6.48 (m, 1H), 5.83-5.75 (m, 1H), 4.34-4.24 (m, 1H), 4.06-3.95 (m, 1H), 2.29-2.15 (m, 2H), 2.07-1.98 (m, 1H), 1.98-1.92 (m, 1H), 1.88-1.75 (m, 2H), 1.67-1.49 (m, 2H) (missing peaks due to water suppression) |
| 9 | 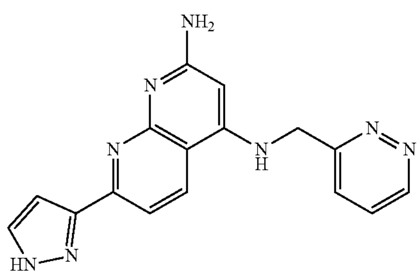 [SMILES: Nc1cc(NCc2cccnn2)c2ccc(-c3cc[nH]n3)nc2n1] | 318.8/ 0.58 min (A)/ 2.0 μM | δ 9.21-9.15 (m, 1H), 8.53-8.42 (m, 1H), 8.00-7.86 (m, 1H), 7.80-7.71 (m, 2H), 7.70-7.66 (m, 1H), 7.66-7.62 (m, 1H), 6.97-6.85 (m, 1H), 6.47-6.29 (m, 1H), 5.70-5.61 (m, 1H), 4.82-4.71 (m, 2H) (missing peaks due to water suppression) |
| 10 | 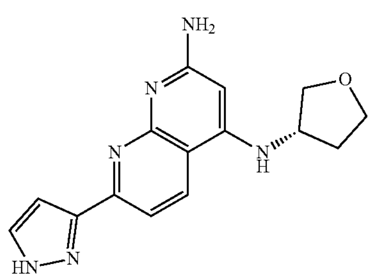 [SMILES: Nc1cc(N[C@H]2CCOC2)c2ccc(-c3cc[nH]n3)nc2n1] | 297.3/ 1.0 min (A)/ 0.93 μM | δ 8.55-8.47 (m, 1H), 7.79-7.71 (m, 1H), 7.69-7.61 (m, 1H), 6.96-6.87 (m, 2H), 6.52-6.43 (m, 1H), 5.80-5.74 (m, 1H), 4.14-4.05 (m, 1H), 4.00-3.84 (m, 2H), 3.82-3.73 (m, 2H), 2.33-2.22 (m, 1H), and 2.08-1.98 (m, 1H) |
| 11 | 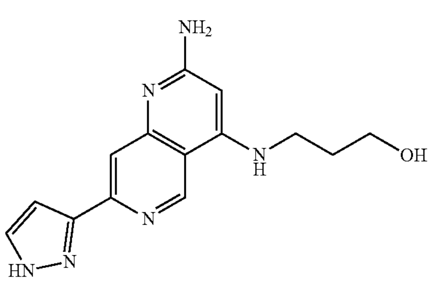 [SMILES: Nc1cc(NCCCO)c2cnc(-c3cc[nH]n3)cc2n1] | 285.2/ 0.44 min (B)/ 1.7 μM | (400 MHz, METHANOL-d4) δ 9.35-9.29 (m, 1H), 7.98-7.89 (m, 2H), 7.85-7.76 (m, 1H), 7.10-7.00 (m, 1H), 4.99-4.87 (m, 2H), 3.17-3.13 (m, 2H), 1.94-1.88 (m, 2H) |

| Ex. No. | Structure | LC/MS [M + H]+/ RT(Method)/ NLRP3 hIL1β EC50 | ¹H NMR (500 MHz, DMSO-d₆, unless otherwise indicated) |
|---|---|---|---|
| 12 | 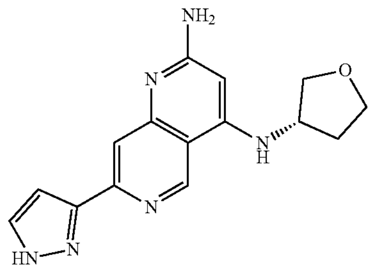 [SMILES: Nc1cc(N[C@H]2CCOC2)c2cnc(-c3cc[nH]n3)cc2n1] | 297.2/ 0.47 min (B)/ 1.7 μM | (400 MHz, METHANOL-d₄) δ 9.51-9.44 (m, 1H), 8.02-7.93 (m, 1H), 7.85-7.80 (m, 1H), 7.15-7.04 (m, 1H), 5.99-5.91 (m, 1H), 3.97-3.91 (m, 2H), 3.50-3.43 (m, 1H), 2.52-2.44 (m, 1H), 2.42-2.35 (m, 1H) |
| 13 | 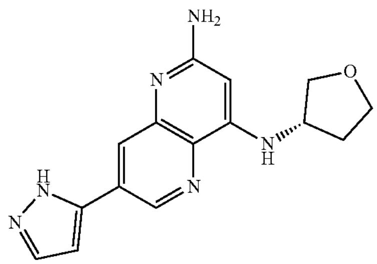 [SMILES: Nc1cc(N[C@H]2CCOC2)c2ncc(-c3ccn[nH]3)cc2n1] | 297.2/ 0.47 min (B)/ 2..3 μM | δ 9.15-9.04 (m, 1H), 8.33-8.23 (m, 1H), 7.97-7.87 (m, 1H), 7.04-6.89 (m, 1H), 6.06-5.93 (m, 1H), 4.30-4.20 (m, 1H), 4.00-3.88 (m, 2H), 3.87-3.76 (m, 2H), 2.35-2.24 (m, 1H), 2.23-2.07 (m, 1H) |
| 14 | 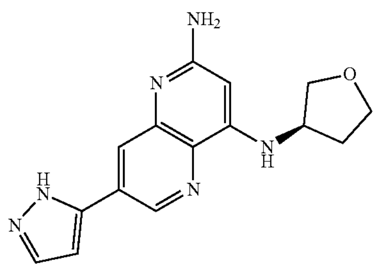 [SMILES: Nc1cc(N[C@@H]2CCOC2)c2ncc(-c3ccn[nH]3)cc2n1] | 297.2/ 0.47 min (B)/ 2.6 μM | δ 9.00-8.83 (m, 1H), 8.13-8.04 (m, 1H), 7.94-7.88 (m, 1H), 6.93-6.87 (m, 1H), 5.94-5.85 (m, 1H), 4.16-4.06 (m, 1H), 3.93-3.82 (m, 2H), 3.77-3.70 (m, 2H), 2.28-2.19 (m, 1H), 2.09-1.96 (m, 1H) |
| 15 | 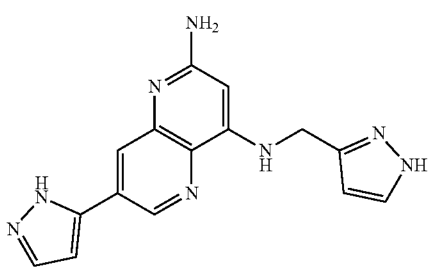 [SMILES: Nc1cc(NCc2cc[nH]n2)c2ncc(-c3ccn[nH]3)cc2n1] | 307.3/ 0.51 min (B)/ 0.28 μM | (400 MHz, METHANOL-d₄) δ 9.17-9.09 (m, 1H), 8.28-8.19 (m, 1H), 7.86-7.79 (m, 1H), 6.99-6.91 (m, 1H). 6.02-5.97 (m, 1H), 5.62-5.57 (m, 1H), 4.51-4.42 (m, 1H), 4.33-4.20 (m, 1H), 2.53-2.38 (m, 1H), 2.29-2.10 (m, 2H), 1.85-1.71 (m, 2H) |
| 16 | 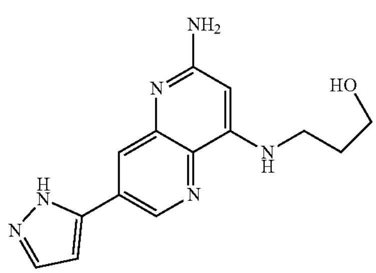 [SMILES: Nc1cc(NCCCO)c2ncc(-c3ccn[nH]3)cc2n1] | 285.2/ 0.93 min (A)/ 0.35 μM | δ 9.16-9.00 (m, 1H), 8.42-8.33 (m, 1H), 8.33-8.24 (m, 1H), 7.04-6.93 (m, 1H), 6.01-5.87 (m, 1H), 3.64-3.53 (m, 2H), 3.48-3.22 (m, 2H), 1.92-1.77 (m, 2H) |

-continued

| Ex. No. | Structure | LC/MS [M + H]+/ RT(Method)/ NLRP3 hIL1β EC50 | ¹H NMR (500 MHz, DMSO-d₆, unless otherwise indicated) |
|---|---|---|---|
| 17 | 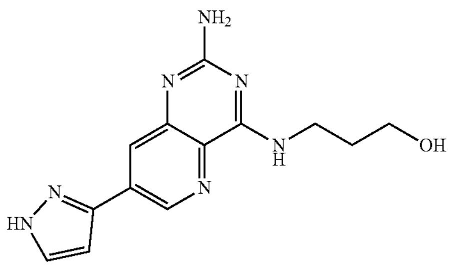 [SMILES: Nc1nc(NCCCO)c2ncc(-c3cc[nH]n3)cc2n1] | 286.0/ 0.97 min (A)/ 0.83 μM | δ 9.45 (br s, 1H), 9.04 (s, 1H), 8.13 (br s, 1H), 7.96-7.81 (m, 1H), 7.00 (d, J = 2.1 Hz, 1H), 3.79-3.59 (m, 2H), 3.53 (br t, J = 6.0 Hz, 2H), 1.82 (quin, J = 6.4 Hz, 2H) |
| 18 | 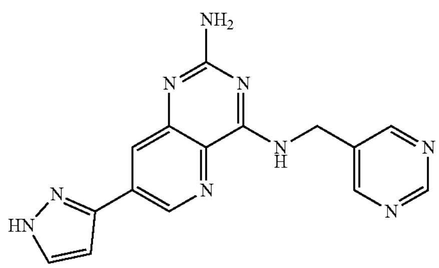 [SMILES: Nc1nc(NCc2cncnc2)c2ncc(-c3cc[nH]n3)cc2n1] | 320.2/ 0.92 min (A)/ 2.0 μM | δ 9.06 (s, 1H), 8.90 (s, 2H), 8.81 (br s, 1H), 8.75 (br t, J = 5.6 Hz, 1H), 7.89 (s, 1H), 7.84 (br d, J = 4.0 Hz, 1H), 6.94 (d, J = 1.5 Hz, 1H), 6.40 (br s, 2H), 4.65 (br d, J = 6.1 Hz, 2H) |
| 19 | 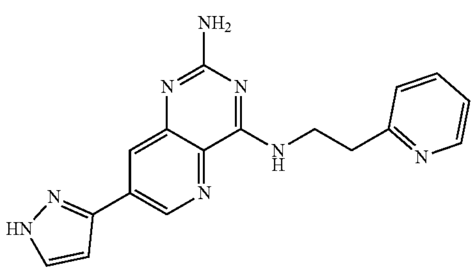 [SMILES: Nc1nc(NCCc2ccccn2)c2ncc(-c3cc[nH]n3)cc2n1] | 333.2/ 1.28 min (A)/ 0.69 μM | δ 8.82 (br s, 1H), 8.51 (br d, J = 4.2 Hz, 1H), 8.35-8.20 (m, 1H), 7.90 (d, J = 1.6 Hz, 1H), 7.87-7.82 (m, 1H), 7.73 (td, J = 7.6, 1.6 Hz, 1H), 7.35 (d, J = 7.7 Hz, 1H), 7.25 (dd, J = 6.7, 5.2 Hz, 1H), 6.94 (d, J = 2.1 Hz, 1H), 6.42 (br s, 2H), 3.84 (q, J = 6.9 Hz, 2H), 3.12 (t, J = 7.4 Hz, 2H) |
| 20 | 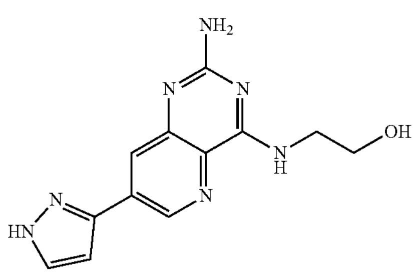 [SMILES: Nc1nc(NCCO)c2ncc(-c3cc[nH]n3)cc2n1] | 272.3/ 0.87 min (A)/ 1.9 μM | δ 8.82 (br s, 1H), 7.98 (br s, 1H), 7.91 (s, 1H), 7.83 (br s, 1H), 6.93 (d, J = 1.5 Hz, 1H), 6.41 (br s, 2H), 3.73-3.50 (m, 3H). The signal between 3-4 ppm was minimized due to the water suppression technique employed. |
| 21 | 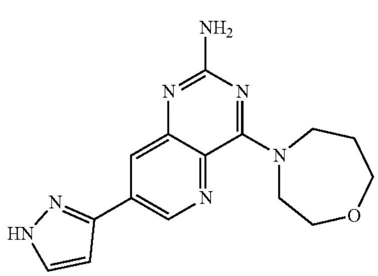 [SMILES: Nc1nc(N2CCCOCC2)c2ncc(-c3cc[nH]n3)cc2n1] | 312.4/ 1.23 min (A)/ 0.70 μM | δ 8.90-8.76 (m, 1H), 7.94 (d, J = 1.5 Hz, 1H), 7.88 (br s, 1H), 6.96 (d, J = 1.8 Hz, 1H), 6.50-6.19 (m, 2H), 4.59-4.16 (m, 2H), 3.81 (t, J = 4.9 Hz, 2H), 3.68 (t, J = 5.5 Hz, 2H), 1.98 (quin, J = 5.8 Hz, 2H) |

| Ex. No. | Structure | LC/MS [M + H]⁺/ RT(Method)/ NLRP3 hIL1β EC50 | ¹H NMR (500 MHz, DMSO-d₆, unless otherwise indicated) |
|---|---|---|---|
| 22 | 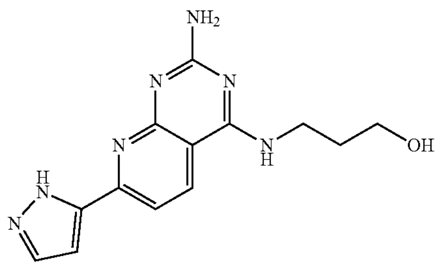 [SMILES: Nc1nc(NCCCO)c2ccc(-c3ccn[nH]3)nc2n1] | 285.2/ 0.73 min (A)/ 3.8 μM | δ 9.57-9.38 (m, 1H), 8.61 (br d, J = 8.5 Hz, 1H), 7.98 (br d, J = 8.2 Hz, 1H), 7.86 (br s, 1H), 6.98-6.89 (m, 1H), 3.67-3.57 (m, 2H), 3.51 (br t, J = 6.1 Hz, 2H), 1.81 (quin, J = 6.6 Hz, 2H) |
| 23 | 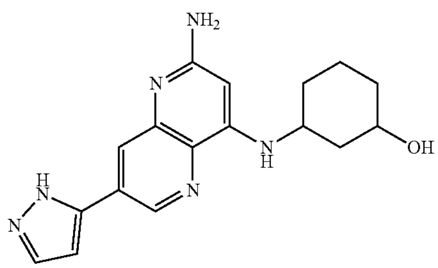 [SMILES: Nc1cc(NC2CCCC(O)C2)c2ncc(-c3ccn[nH]3)cc2n1] | 325.2/ 0.88 min (A)/ 2..3 μM | δ 9.08-9.01 (m, 1H), 8.28-8.18 (m, 2H), 7.93-7.85 (m, 1H). 7.80-7.70 (m, 2H), 7.00-6.92 (m, 1H), 5.96-5.88 (m, 1H), 3.73-3.47 (m, 3H), 2.09-1.99 (m, 2H), 1.80-1.67 (m, 3H), 1.61-1.44 (m, 2H), 1.38-1.19 (m, 2H) |
| 24 | 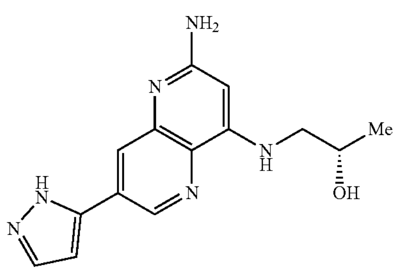 [SMILES: C[C@H](O)CNc1cc(N)nc2cc(-c3ccn[nH]3)cnc12] | 285.1/ 0.97 min (A)/ 0.31 μM | δ 9.08-8.92 (m, 1H), 8.33-8.09 (m, 1H), 7.96-7.80 (m, 1H), 7.79-7.59 (m, 1H), 7.55-7.22 (m, 2H), 7.03-6.85 (m, 1H), 6.04-5.79 (m, 1H), 5.14-4.95 (m, 1H), 3.99-3.88 (m, 1H), 3.63-3.44 (m, 1H), 3.43-3.32 (m, 1H), 3.29-3.06 (m, 1H), 1.12 (d, J = 6.1 Hz, 3H) |
| 25 | 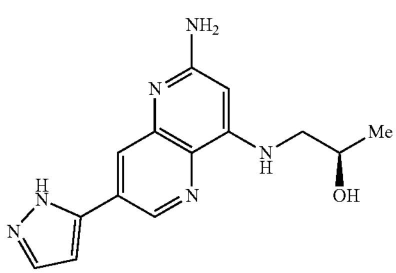 [SMILES: C[C@@H](O)CNc1cc(N)nc2cc(-c3ccn[nH]3)cnc12] | 285.1/ 0.70 min (A)/ 0.08 μM | δ 8.83-8.71 (m, 1H), 8.00-7.90 (m, 1H), 7.81-7.69 (m, 1H), 6.87-6.80 (m, 1H), 6.80-6.71 (m, 1H), 6.25-6.13 (m, 2H), 5.84-5.77 (m, 1H), 3.97-3.85 (m, 1H), 3.78-3.42 (m, 1H), 3.21-2.92 (m, 3H), 1.12 (d, J = 6.2 Hz, 3H) |
| 26 | 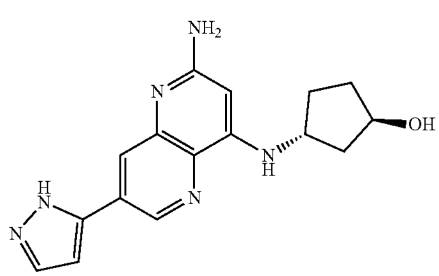 [SMILES: Nc1cc(N[C@@H]2CC[C@@H](O)C2)c2ncc(-c3ccn[nH]3)cc2n1] | 311.1/ 0.80 min (A)/ 0.59 μM | δ 8.83-8.75 (m, 1H), 8.02-7.94 (m, 1H), 7.86-7.75 (m, 1H), 6.92-6.84 (m, 1H), 6.54 (br d, J = 7.0 Hz, 1H), 6.32-6.17 (m, 2H), 5.92-5.84 (m, 1H), 4.03-3.96 (m, 1H), 3.68-3.39 (m, 1H), 2.27-2.17 (m, 1H), 2.06-1.91 (m, 2H), 1.83-1.74 (m, 1H), 1.62-1.50 (m, 2H) |

| Ex. No. | Structure | LC/MS [M + H]+/ RT(Method)/ NLRP3 hIL1β EC50 | 1H NMR (500 MHz, DMSO-d6, unless otherwise indicated) |
|---|---|---|---|
| 27 | 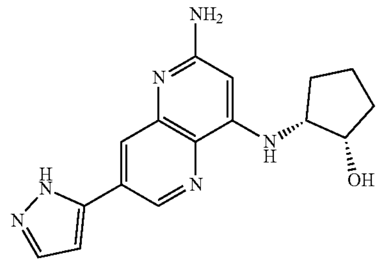 [SMILES: Nc1cc(N[C@@H]2CCC[C@@H]2O)c2ncc(-c3ccn[nH]3)cc2n1] | 309.3/ 1.09 min (A)/ 0.44 μM | δ 8.89-8.71 (m, 1H), 8.07-7.91 (m, 1H), 7.87-7.69 (m, 1H), 6.99-6.80 (m, 2H), 6.33-6.10 (m, 2H), 5.95-5.78 (m, 1H), 4.28-4.07 (m, 1H), 3.73-3.50 (m, 1H), 2.15-2.05 (m, 1H), 1.89-1.73 (m, 2H), 1.71-1.61 (m, 1H), 1.60-1.48 (m, 2H) |
| 28 | 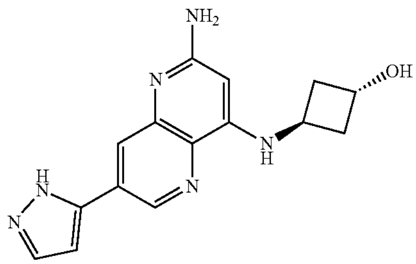 [SMILES: Nc1cc(N[C@H]2C[C@H](O)C2)c2ncc(-c3ccn[nH]3)cc2n1] | 297.0/ 0.99 min (A)/ 0.14 μM | δ 9.08 (s, 1H), 8.34 (br d, J = 5.2 Hz, 1H), 8.29-8.22 (m, 1H), 7.98-7.81 (m, 3H), 6.97 (d, J = 2.1 Hz, 1H), 5.75 (s, 1H), 4.42-4.30 (m, 1H), 4.18-4.04 (m, 1H), 2.49-2.45 (m, 2H), 2.33-2.22 (m, 2H) |
| 29 | 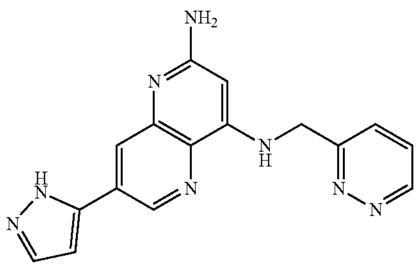 [SMILES: Nc1cc(NCc2cccnn2)c2ncc(-c3ccn[nH]3)cc2n1] | 319.1/ 0.95 min (A)/ 0.28 μM | δ 9.19-9.15 (m, 1H), 8.89 (s, 1H), 8.02 (s, 1H), 7.89 (br t, J = 5.7 Hz, 1H), 7.85-7.80 (m, 1H), 7.71-7.64 (m, 2H), 6.92 (d, J = 1.2 Hz, 1H), 6.26 (br. s, 2H), 5.80 (s, 1H), 4.80 (d, J = 6.1 Hz, 2H), 1.92 (s, 3H) |
| 30 | 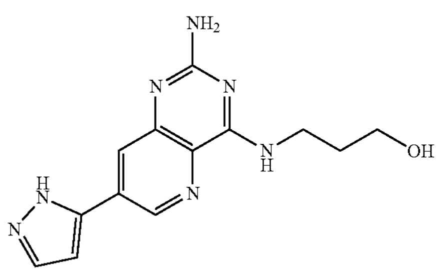 [SMILES: Nc1nc(NCCCO)c2ncc(-c3ccn[nH]3)cc2n1] | 284.3/ 1.22 min (A)/ 1.50 μM | δ 9.57 (br s, 1H), 9.05 (s, 1H), 8.14 (br s, 1H), 7.91 (br s, 1H), 7.01 (d, J = 1.3 Hz, 1H), 2.64 (s, 1H), 1.63 (br t, J = 7.3 Hz, 2H), 1.45-1.26 (m, 2H), 0.91 (t, J = 7.4 Hz, 3H) Three proton is not visible, likely due to overlap with suppressed water peak. |
| 31 | 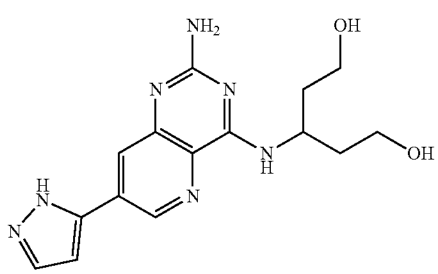 [SMILES: Nc1nc(NC(CCO)CCO)c2ncc(-c3ccn[nH]3)cc2n1] | 328.1/ 1.12 min (A)/ 2.0 μM | δ 8.79 (br s, 1H), 7.93-7.79 (m, 2H), 7.69 (br d, J = 9.4 Hz, 1H), 6.92 (d, J = 2.2 Hz, 1H), 6.25 (br s, 2H), 3.85-3.68 (m, 1H), 3.49-3.37 (m, 1H), 1.76 (q, J = 6.6 Hz, 2H), 1.67-1.49 (m, 2H), 1.40-1.22 (m, 2H), 0.88 (t, J = 7.3 Hz, 3H) One proton is not visible, likely due to overlap with suppressed water peak. |

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula (I):

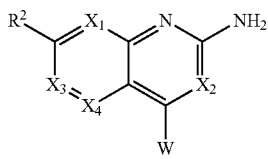

or a stereoisomer, a tautomer, or a pharmaceutically acceptable salt thereof, wherein:
W is independently selected from: —Y—$R^6$, -Q-Y—$R^6$, -Q-$R^{6a}$, and $R^{6b}$;
Q is independently selected from: $NR^5$, $CHR^5$, O, and S;
Y is independently selected from: $C_{1-10}$ alkylene, $C_{2-10}$ alkenylene, and $C_{2-10}$ alkynylene, each of which is substituted with 0 to 4 $R^e$ and/or each of which is optionally interrupted by one of the following:
(i) O;
(ii) $N(R^f)$;
(iii) $C_{3-6}$ cycloalkylene substituted with 0 to 4 $R^g$;
(iv) phenylene further substituted with 0 to 4 $R^d$,
(v) heteroarylene including from 5 to 10 ring atoms, wherein from 1 to 4 ring atoms are each independently selected from N, $N(R^f)$, O, and S, and which is substituted with 0 to 4 $R^d$; or
(vi) heterocycloalkylene including from 3 to 10 ring atoms, wherein from 1 to 3 ring atoms are each independently selected from N, $N(R^f)$, O and $S(O)_{1-2}$, and which is substituted with 0 to 4 $R^g$;
$X_1$ and $X_2$ are, at each occurrence, independently N or $CR^1$;
$X_3$ is independently N or $CR^3$;
$X_4$ is independently N or $CR^4$;
provided that at least one of $X_1$, $X_3$ and $X_4$ is N and no more than two of $X_1$, $X_3$ and $X_4$ are N;
$R^1$ and $R^3$ are, at each occurrence, independently selected from: H, halogen, cyano, $C_{1-4}$ alkyl, $C_{1-4}$ haloalkyl, $C_{1-4}$ alkoxy, and $C_{1-4}$ haloalkoxy;
$R^2$ is independently a heteroaryl including 5 ring atoms, wherein from 1 to 4 ring atoms are each independently selected from N, NH, O, and S, wherein the heteroaryl is substituted with 0 to 3 $R^d$;
$R^4$ is independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and —($C_{0-3}$ alkylene)-heteroaryl including 5 ring atoms, wherein from 1 to 4 ring atoms are each independently selected from N, NH, $N(C_{1-4}$ alkyl), O, and S, wherein the heteroaryl is substituted with 0 to 3 $R^d$;
$R^5$ is independently H or $C_{1-4}$ alkyl;
$R^6$ is independently selected from: —$OR^a$, $C_{1-4}$ haloalkoxy, —C(O)$R^a$, —$CO_2R^a$, —$SO_{1-2}(R^h)$, —$CONR^iR^j$, cyano and $R^{6a}$;
$R^{6a}$ is independently selected from: phenyl substituted with 0 to 4 $R^d$; heteroaryl including from 5 to 10 ring atoms, wherein from 1 to 4 ring atoms are each independently selected from N, $N(R^f)$, O, and S, wherein the heteroaryl is substituted with 0 to 4 $R^d$; $C_{3-10}$ cycloalkyl substituted with 0 to 4 $R^g$; and heterocyclyl including from 3 to 10 ring atoms, wherein from 1 to 3 ring atoms are each independently selected from N, $N(R^f)$, O and $S(O)_{1-2}$, wherein the heterocyclyl is substituted with 0 to 4 $R^g$;
$R^{6b}$ is independently selected from: $C_{1-6}$ alkoxy, $C_{1-4}$ haloalkoxy, —C(O)$R^a$, —$CO_2R^a$, —$SO_{1-2}(R^h)$, —$CONR^iR^j$, phenyl substituted with 0 to 4 $R^d$; heteroaryl including from 5 to 10 ring atoms, wherein from 1 to 4 ring atoms are each independently selected from N, $N(R^f)$, O, and S, wherein the heteroaryl is substituted with 0 to 4 $R^d$; $C_{3-10}$ cycloalkyl substituted with 0 to 4 $R^g$; and heterocyclyl selected from

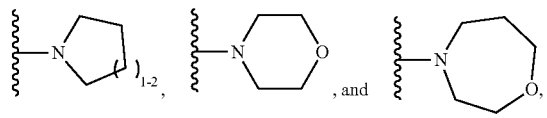

wherein the heterocyclyl is substituted with 0 to 2 $R^g$;
$R^a$ is independently selected from: H; $C_{1-8}$ alkyl substituted with 0 to 2 $R^e$; —($C_{0-3}$ alkylene)-$C_{3-10}$ cycloalkyl, wherein the cycloalkyl is substituted with 0 to 4 $R^g$; —($C_{0-3}$ alkylene)-heterocyclyl including from 3 to 10 ring atoms, wherein from 1 to 3 ring atoms are each independently selected from $N(R^f)$, O, and S, wherein the heterocyclyl is substituted with 0 to 4 $R^g$; —($C_{0-3}$ alkylene)-($C_{6-10}$ aryl), wherein the aryl is substituted with 0 to 4 $R^d$, and —($C_{0-3}$ alkylene)-heteroaryl including from 5 to 10 ring atoms, wherein from 1 to 4 ring atoms are each independently selected from N, $N(R^f)$, O, and S, wherein the heteroaryl is substituted with 0 to 4 $R^d$;
$R^b$ and $R^c$ are, at each occurrence, independently $R^a$ or —C(O)$R^a$;
$R^d$ is independently selected from: halogen, OH, cyano, $C_{1-4}$ alkoxy, $C_{1-4}$ alkoxy, $C_{1-4}$ haloalkyl, $C_{1-4}$ haloalkoxy, —C(O)O($C_{1-4}$ alkyl), $NH_2$, $N(C_{1-4}$ alkyl$)_2$, —C(O)$NH_2$, —C(O)N($C_{1-4}$ alkyl$)_2$, $C_{2-6}$ alkenyl, $C_{2-6}$ alkynyl, and $C_{1-6}$ alkyl substituted with 0 to 2 $R^e$;
$R^e$ is independently selected from: F, OH, cyano, $C_{1-4}$ alkoxy, $C_{1-4}$ haloalkyl, $C_{1-4}$ haloalkoxy, and $C_{1-4}$ alkyl substituted with 0 to 1 $R^n$;
$R^f$ is independently selected from: H, $C_{1-4}$ alkyl substituted with 0 to 1 OH, —C(O)($C_{1-4}$ alkyl), and —C(O)O($C_{1-4}$ alkyl);
$R^g$ is independently oxo or $R^d$,
$R^h$ is independently selected from: $C_{1-6}$ alkyl, $C_{1-4}$ haloalkyl, —($C_{0-3}$ alkylene)-phenyl, and —($C_{0-3}$ alkylene)-heteroaryl including from 5 to 6 ring atoms, wherein from 1-4 ring atoms are each independently selected from N, $N(R^f)$, O, and S;
$R^i$ and $R^j$ are, at each occurrence, independently H or $R^h$; or $R^i$ and $R^j$ together with the nitrogen atom to which each is attached forms a ring including from 5 to 6 ring atoms, wherein the ring includes: (a) from 3 to 5 ring carbon atoms, each of which is substituted with 1 to 2 substituents independently H and $R^m$; and (b) from 0 to 2 ring heteroatoms (in addition to the nitrogen atom attached to $R^i$ and $R^j$), which are each independently selected from $N(R^f)$, O, and S;
$R^m$ is independently oxo or $R^e$; and
$R^n$ is independently selected from: OH, $CONH_2$ and $C_{1-4}$ alkoxy.

2. The compound of claim 1, wherein:

Q is independently selected from: NH, N(C$_{1-4}$ alkyl), CH$_2$, and O;

Y is independently selected from: C$_{1-10}$ alkylene, C$_{2-6}$ alkenylene, and C$_{2-6}$ alkynylene, each of which is substituted with 0 to 4 R$^e$ and/or each of which is optionally interrupted by one of the following:
(i) O;
(ii) N(R$^f$);
(iii) C$_{3-6}$ cycloalkylene substituted with 0 to 4 R$^g$;
(iv) phenylene substituted with 0 to 4 R$^d$;
(v) heteroarylene including from 5 to 6 ring atoms, wherein from 1 to 4 ring atoms are each independently selected from N, N(R$^f$), O, and S, and which is substituted with 0 to 4 R$^d$; or
(vi) heterocycloalkylene including from 3 to 7 ring atoms, wherein from 1 to 3 ring atoms are each independently selected from N, N(R$^f$), O and S(O)$_{1-2}$, and which is substituted with 0 to 4 R$^g$;

R$^2$ is independently 5-membered heteroaryl including from 1 to 2 ring atoms are each independently selected from N, NH, O, and S;

R$^4$ is independently selected from: H, halogen, cyano, C$_{1-4}$ alkyl, C$_{1-4}$ haloalkyl, C$_{1-4}$ alkoxy, C$_{1-4}$ haloalkoxy, N(C$_{1-4}$ alkyl)$_2$, and 5-membered heteroaryl including from 1 to 2 ring atoms are each independently selected from N, NH, O, and S;

R$^a$ is independently selected from: H, C$_{1-6}$ alkyl substituted with 0 to 2 R$^e$, and benzyl;

R$^h$ is independently C$_{1-6}$ alkyl or benzyl; and

R$^i$ and R$^j$ are, at each occurrence, independently H or R$^h$.

3. The compound of claim 2, wherein the compound is of Formula (II):

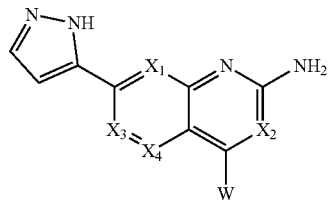

(II)

or a stereoisomer, a tautomer, or a pharmaceutically acceptable salt thereof, wherein:

W is independently selected from: —Y—R$^6$, —O—R$^{6a}$, —NH—R$^{6a}$, —O—Y—R$^6$, —NH—Y—R$^6$, and R$^{6b}$;

Y is independently C$_{1-8}$ alkylene or C$_{2-6}$ alkynylene, each of which is substituted with 0 to 4 R$^e$;

X$_1$ and X$_2$ are, at each occurrence, independently N or CR$^1$;

X$_3$ is independently N or CR$^3$;

X$_4$ is independently N or CR$^4$;

provided that only one of X$_1$, X$_3$ and X$_4$ is N;

R$^1$, R$^3$ and R$^4$ are, at each occurrence, independently selected from: H, halogen and C$_{1-4}$ alkyl;

R$^6$ is independently selected from: H, OH, C$_{1-6}$ alkoxy, N(C$_{1-4}$ alkyl)$_2$, C$_{1-6}$ haloalkyl, cyano, and R$^{6a}$;

R$^{6a}$ is independently selected from: phenyl substituted with 0 to 3 R$^d$; heteroaryl including from 5 to 10 ring atoms, wherein from 1 to 4 ring atoms are each independently selected from N, N(R$^f$), O, and S, wherein the heteroaryl is substituted with 0 to 3 R$^d$; C$_{3-6}$ cycloalkyl substituted with 0 to 3 R$^g$; heterocyclyl including from 3 to 8 ring atoms, wherein from 1 to 3 ring atoms are each independently selected from N, N(R$^f$), O and S(O)$_{1-2}$, wherein the heterocyclyl is substituted with 0 to 3 R$^g$; and

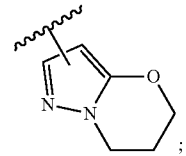

R$^{6b}$ is independently selected from: C$_{1-6}$ haloalkyl, cyano, phenyl substituted with 0 to 4 R$^d$; heteroaryl including from 5 to 10 ring atoms, wherein from 1 to 4 ring atoms are each independently selected from N, N(R$^f$), O, and S, wherein the heteroaryl is substituted with 0 to 4 R$^d$; C$_{3-10}$ cycloalkyl substituted with 0 to 4 R$^g$; and heterocyclyl selected from

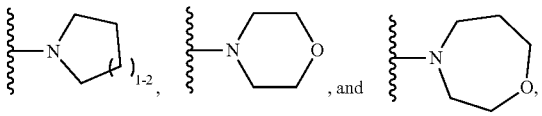

wherein the heterocyclyl is substituted with 0 to 2 R$^g$;

R$^d$ is independently selected from: halogen, cyano, OH, CH$_2$OH, C$_{1-4}$ alkoxy, C$_{1-4}$ haloalkyl, N(C$_{1-4}$ alkyl)$_2$, and C$_{1-4}$ alkyl substituted with 0 to 2 C$_{1-4}$ alkoxy;

R$^e$ is independently selected from: F, OH, —(CH$_2$)$_{1-4}$OH, —CH$_2$CONH$_2$ and C$_{1-4}$ alkyl substituted with 1 C$_{1-4}$ alkoxy;

R$^f$ is independently H or C$_{1-4}$ alkyl; and

R$^g$ is independently oxo or R$^d$.

4. The compound of claim 3, wherein:

W is independently selected from: —Y—R$^6$, —NH—R$^{6a}$, —NH—Y—R$^6$, R$^{6b}$, and

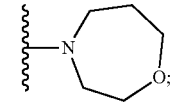

Y is independently C$_{1-6}$ alkylene substituted with 0 to 1 R$^e$;

X$_1$ and X$_2$ are, at each occurrence, independently N or CH;

X$_3$ is independently N or CH;

X$_4$ is independently N or CH;

provided that only one of X$_1$, X$_3$ and X$_4$ is N;

R$^6$ is independently selected from: H, OH, C$_{1-6}$ alkoxy, CN, C$_{1-6}$ haloalkyl, and R$^{6a}$;

R$^{6a}$ is independently selected from: pyrazolyl, pyridyl, pyrimidinyl, pyrazinyl, pyridazinyl, C$_{3-6}$ cycloalkyl and

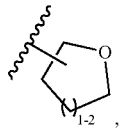

wherein each ring moiety is substituted with 0 to 2 R$^g$;

R$^{6b}$ is independently 5-membered heteroaryl, wherein from 1 to 4 ring atoms are each independently selected from N, NH, O, and S, wherein the heteroaryl is substituted with 0 to 2 $R^d$; $C_{3-6}$ cycloalkyl substituted with 0 to 2 $R^8$; and $R^e$ is independently F or OH.

5. The compound of claim 4, wherein:

W is independently selected from: —NH—$R^{6a}$, —NH—Y—$R^6$,

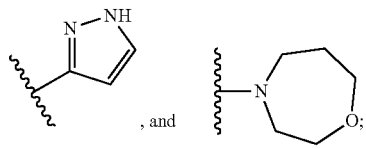 [SMILES: *c1cc[nH]n1 ; *N1CCCOCC1], and

Y is independently $C_{1-4}$ alkylene;

$R^6$ is independently selected from: OH, $OCH_3$ and $R^{6a}$, $R^{6a}$ is independently selected from: pyrazolyl, pyridyl, pyrimidinyl, cyclopentyl substituted with OH; and

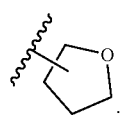.

6. The compound of claim 5, wherein:

W is independently selected from: —$NH(CH_2)_{2-4}OH$,

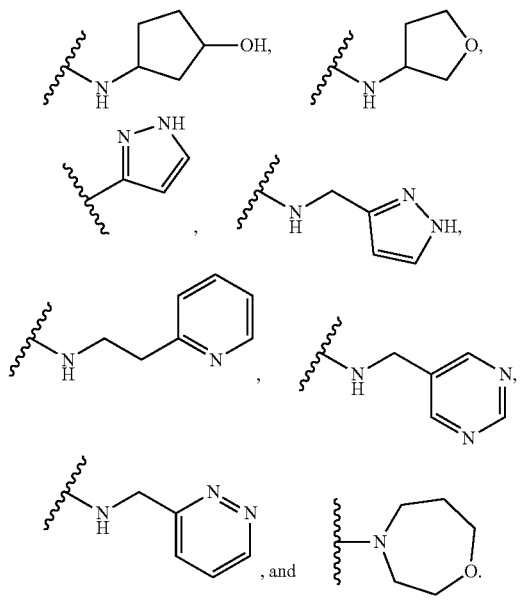

7. A compound according to claim 1, wherein the compound is selected from Examples 1 to 31 or a pharmaceutically acceptable salt thereof.

8. A pharmaceutical composition comprising a compound or a pharmaceutically acceptable salt thereof as claimed in claim 7 and one or more pharmaceutically acceptable excipients.

9. A method of treating cancer, comprising administering to a subject in need of such treatment an effective amount of a compound or a pharmaceutically acceptable salt thereof as claimed in claim 1.

10. The method of claim 9, wherein the cancer is selected from acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

11. The method of claim 9, wherein the cancer is selected from breast cancer, colon cancer, rectal cancer, colorectal cancer, pancreatic cancer, and prostate cancer.

12. The method of claim 9, wherein the cancer is selected from hormone receptor positive breast cancer, microsatellite stable colon or rectal cancer, pancreatic cancer and prostate cancer.

13. The method of claim 9, wherein the compound is administered in combination with one or more additional cancer therapies.

14. The method of claim 13, wherein the one or more additional cancer therapies comprise surgery, radiotherapy, chemotherapy, toxin therapy, immunotherapy, cryotherapy or gene therapy, or a combination thereof.

15. The method of claim 13, wherein the additional cancer therapy comprises one or more agents selected from nivolumab, pembrolizumab, PDR001, MEDI-0680, cemiplimab, JS001, BGB-A317, INCSHR1210, TSR-042, GLS-010, AM-0001, STI-1110, AGEN2034, MGD013, IBI308, BMS-936559, atezolizumab, durvalumab, avelumab, STI-1014, CX-072, LY3300054, CK-301, urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab, MK-1308, AGEN-1884, and tremelimumab.

16. The method of claim 13, wherein the additional cancer therapy comprises one or more agents selected from nivolumab, ipilimumab, pembrolizumab, atezolizumab, durvalumab and avelumab.

* * * * *

UNITED STATES PATENT AND TRADEMARK OFFICE
CERTIFICATE OF CORRECTION

PATENT NO. : 12,150,937 B2
APPLICATION NO. : 17/422252
DATED : November 26, 2024
INVENTOR(S) : Scott Watterson et al.

It is certified that error appears in the above-identified patent and that said Letters Patent is hereby corrected as shown below:

In the Claims

Column 69
Line 29, Claim 1, "$R^8$" should read -- $R^g$ --; and
Line 38, Claim 1, "$R^8$" should read -- $R^g$ --.

Column 71
Line 66, Claim 3, "$R^8$" should read -- $R^g$ --.

Column 73
Line 3, Claim 4, "$R^8$" should read -- $R^g$ --.

Signed and Sealed this
Fourth Day of February, 2025

Coke Morgan Stewart
*Acting Director of the United States Patent and Trademark Office*